(12) United States Patent
Dukesherer et al.

(10) Patent No.: US 7,906,536 B2
(45) Date of Patent: Mar. 15, 2011

(54) PROCESSES FOR THE PREPARATION OF 3-(4-(2,4-DIFLUOROBENZYLOXY)-3-BROMO-6-METHYL-2-OXOPYRIDIN-1(2H)-YL)-N,4-DIMETHYLBENZAMIDE

(75) Inventors: Daniel Dukesherer, Saint Louis, MO (US); Michael Mao, Chesterfield, MO (US); Richard Vonder Embse, Saint Louis, MO (US); Gopi Yalamanchili, Saint Louis, MO (US); Rajappa Vaidyanathan, Groton, CT (US); Brian Chekal, Niantic, CT (US); George Klemm, Webster Groves, MO (US); Ronald VanderRoest, Kalamazoo, MI (US); Randy Geurink, Caledonia, MI (US)

(73) Assignee: Pfizer Inc, New York, NY (US)

( * ) Notice: Subject to any disclaimer, the term of this patent is extended or adjusted under 35 U.S.C. 154(b) by 665 days.

(21) Appl. No.: 11/954,883

(22) Filed: Dec. 12, 2007

(65) Prior Publication Data

US 2008/0177077 A1    Jul. 24, 2008

Related U.S. Application Data

(60) Provisional application No. 60/869,748, filed on Dec. 13, 2006.

(51) Int. Cl.
*A61K 31/44* (2006.01)
(52) U.S. Cl. ...................................................... 514/348
(58) Field of Classification Search .................. 514/348
See application file for complete search history.

(56) References Cited

FOREIGN PATENT DOCUMENTS

| WO | WO03068230 | 8/2003 |
|----|------------|--------|
| WO | WO 03/068230 | 12/2003 |
| WO | WO2007/091176 | 8/2007 |

*Primary Examiner* — Rita J Desai
*Assistant Examiner* — John Mabry
(74) *Attorney, Agent, or Firm* — Jennifer A. Kispert; Robert T. Ronau

(57) ABSTRACT

This invention is directed generally to processes for the preparation of compounds of Formula I:

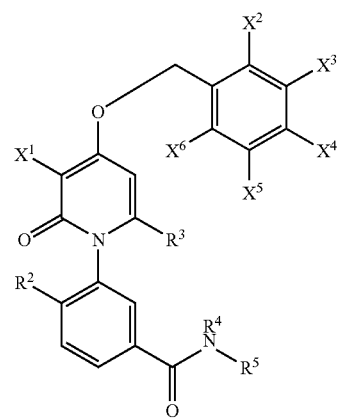

wherein $R^2$, $R^3$, $R^4$, $R^5$, $X^1$, $X^2$, $X^3$, $X^4$, $X^5$, $X^6$ are as defined in the specification.

10 Claims, No Drawings

PROCESSES FOR THE PREPARATION OF 3-(4-(2,4-DIFLUOROBENZYLOXY)-3-BROMO-6-METHYL-2-OXOPYRIDIN-1 (2H)-YL)-N,4-DIMETHYLBENZAMIDE

BACKGROUND 3-(4-(2,4-difluorobenzyloxy)-3-bromo-6-methyl-2-oxopyridin-1(2H)-yl)-N,4-dimethylbenzamide is known to be useful as therapeutic agent for treating many pathological conditions, including the treatment or prevention of inflammatory and respiratory diseases. The efficacy of 3-(4-(2,4-difluorobenzyloxy)-3-bromo-6-methyl-2-oxopyridin-1 (2H)-yl)-N,4-dimethylbenzamide is believed to be related to its ability to inhibit p38 kinase.

It is believed that p38α kinase can cause or contribute to the effects of, for example, inflammation generally; arthritis; neuroinflammation; pain; fever; pulmonary disorders; cardiovascular diseases; cardiomyopathy; stroke; ischemia; reperfusion injury; renal reperfusion injury; brain edema; neurotrauma and brain trauma; neurodegenerative disorders; central nervous system disorders; liver disease and nephritis; gastrointestinal conditions; ulcerative diseases; ophthalmic diseases; opthalmological conditions; glaucoma; acute injury to the eye tissue and ocular traumas; diabetes; diabetic nephropathy; skin-related conditions; viral and bacterial infections; myalgias due to infection; influenza; endotoxic shock; toxic shock syndrome; autoimmune disease; bone resorption diseases; multiple sclerosis; disorders of the female reproductive system; pathological (but non-malignant) conditions, such as hemaginomas, angiofibroma of the nasopharynx, and avascular necrosis of bone; benign and malignant tumors/neoplasia including cancer; leukemia; lymphoma; systemic lupus erthrematosis (SLE); angiogenesis including neoplasia; and metastasis.

WO03/068,230A1, published on Aug. 21, 2003, describes 3-(4-(2,4-difluorobenzyloxy)-3-bromo-6-methyl-2-oxopyridin-1(2H)-yl)-N,4-dimethylbenzamide, its preparation and use in the treatment of inflammation.

3-(4-(2,4-difluorobenzyloxy)-3-bromo-6-methyl-2-oxopyridin-1(2H)-yl)-N,4-dimethylbenzamide and closely related analogs can be made by either the following described racemic route (Route 1) or chiral route (Route 2).

In efforts to make the discovery route more efficient and a scalable process, several modifications have been introduced in Route 1. These not only include improved reaction conditions and workup procedures but also new reactions. The sequence of steps 2, 3, and 4 of the discovery route-alkylation, hydrolysis and bromination- was changed to bromination, alkylation and hydrolysis for a variety of reasons. These include avoiding tedious workup at each step, such as multiple extractions and concentrations and to obtain higher yields. Route 1 avoids the use of costly materials where possible.

Route 2 was initiated to develop a novel chiral route towards the preparation of a compound of Formula I to eliminate the need for chiral chromatography. An efficient and scalable chiral synthesis was identified by utilizing a selective enzymatic hydrolysis approach. Route 2 also avoids the use of costly materials where possible.

SUMMARY

The first embodiment of the present invention is an improved process for the preparation of a compound of Formula I:

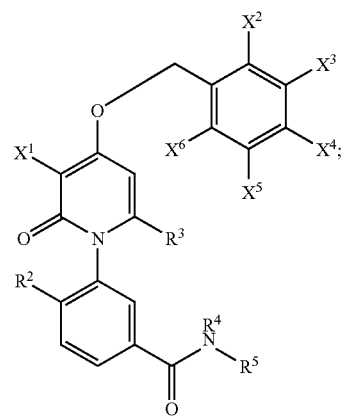

comprising the steps of:

a) contacting a compound of Formula V:

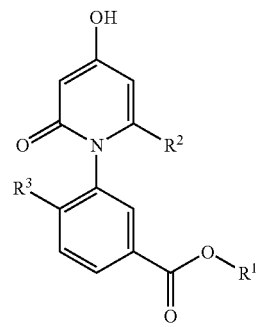

with a halogenating reagent in the presence of at least one solvent to produce a compound of Formula IV:

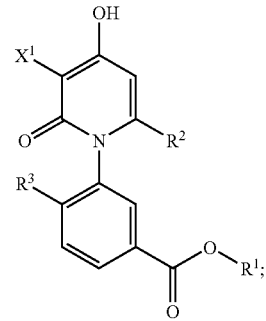

b) contacting a compound of Formula IV with a substituted benzylhalide in the presence of at least one solvent and a base to produce a compound of Formula III:

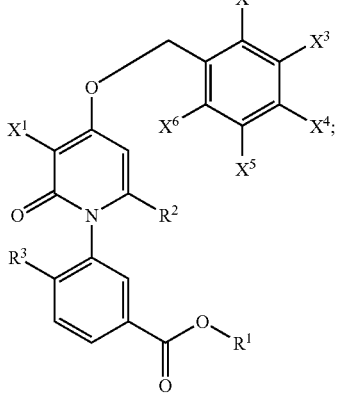

c) contacting a compound of Formula III with a base in the presence of at least one solvent to produce a compound of Formula II:

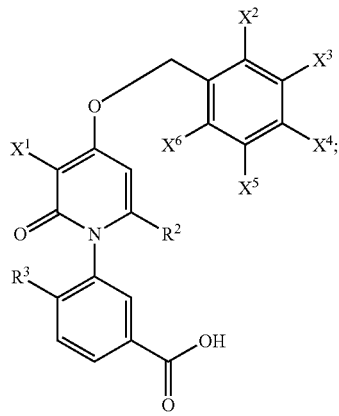

II d) contacting a compound of Formula II with a activating reagent in the presence of at least one solvent and then contacting the resulting mixture with an amine to produce a compound of Formula I;

wherein $X^1$, $X^2$, $X^3$, $X^4$, $X^5$ and $X^6$ are independently H, halo, or a $C_1$-$C_6$ alkyl;

$R^1$ is a $C_1$-$C_6$ alkyl or aryl;

$R^2$ is H, halo, or a $C_1$-$C_6$ alkyl;

$R^3$ is halo, or a $C_1$-$C_6$ alkyl; and $R^4$ is H or a $C_1$-$C_6$ alkyl;

$R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

The second embodiment of the present invention is an improved process for the preparation of a compound of Formula I comprising the steps:

a) contacting a compound of formula V:

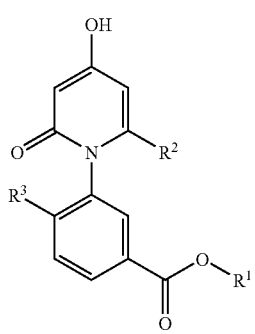

V with a halogenating reagent in the presence of at least one solvent to produce a compound of Formula IV:

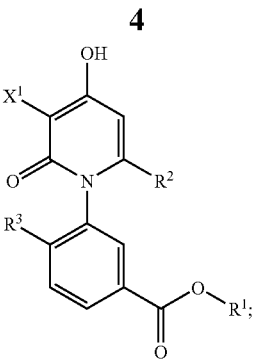

IV b) contacting a compound of Formula IV with an hydrolase in the presence of a buffer solution to produce a compound of Formula X:

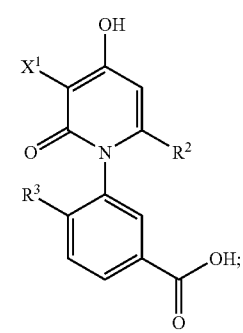

X c) contacting a compound of Formula X with a activating reagent in the presence of at least one solvent and then contacting the resulting mixture with an amine to produce a compound of Formula IX:

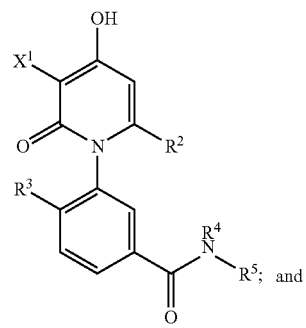

IX d) contacting a compound of Formula IX with a substituted benzylhalide in the presence of a base and at least one solvent to produce a compound of Formula I;

wherein $X^1$, $X^2$, $X^3$, $X^4$, $X^5$ and $X^6$ are independently H, halo, or a $C_1$-$C_6$ alkyl;

$R^1$ is a $C_1$-$C_6$ alkyl or aryl;

$R^2$ is H, halo, or a $C_1$-$C_6$ alkyl;

$R^3$ is halo, or a $C_1$-$C_6$ alkyl; and $R^4$ is H or a $C_1$-$C_6$ alkyl;

$R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

The third embodiment of the present invention is an improved process for the preparation of a compound of Formula I having the following structure:

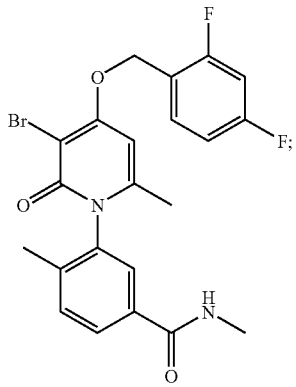

comprising the steps:

a) contacting a compound of Formula V having the following structure:

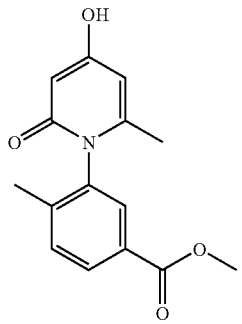

with 1,3-dibromo-5,5-dimethylhydantoin in the presence of acetonitrile to produce a compound of Formula IV having the following structure:

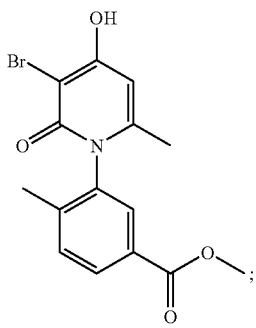

b) contacting a compound of Formula IV with *Bacillus* sp. protease in the presence of a dibasic potassium phosphate buffer solution to produce a compound of Formula X having the following structure:

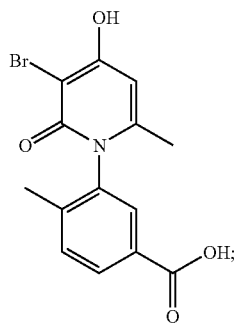

c) contacting a compound of Formula X with 1,1'-carbonyl-diimidazole in the presence of dimethylformamide and then the resulting mixture is contacted with $NH_2CH_3$ in tetrahydrofuran to produce a compound of Formula IX having the following structure:

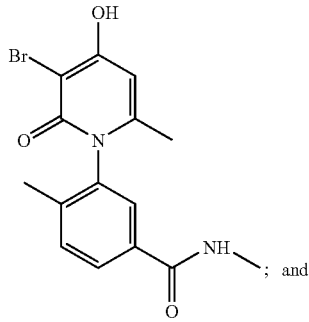
; and d) contacting a compound of Formula IX with a compound having the following structure:

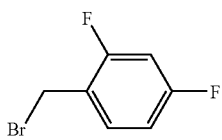

in the presence of potassium carbonate and N-methylpyrrolidinone.

The fourth embodiment of the present invention provides novel intermediates selected from methyl 3-(3-bromo-4-hydroxy-6-methyl-2-oxopyridin-1(2H)-yl)-4-methylbenzoate;

(+)-methyl 3-(3-bromo-4-hydroxy-6-methyl-2-oxopyridin-1(2H)-yl)-4-methylbenzoate;

3-(3-bromo-4-hydroxy-6-methyl-2-oxopyridin-1(2H)-yl)-N,4-dimethylbenzamide 3-(3-bromo-4-hydroxy-6-methyl-2-oxopyridin-1(2H)-yl)-4-methyl benzoic acid;

(−)-3-(3-bromo-4-hydroxy-6-methyl-2-oxopyridin-1(2H)-yl)-4-methylbenzoic acid; and (−)-1-(5-(1H-imidazole-1-carbonyl)-2-methylphenyl)-3-bromo-4-hydroxy-6-methylpyridin-2(1H)-one, or a pharmaceutically acceptable salt thereof.

DETAILED DESCRIPTION

The compound and salts of this invention can be prepared from materials generally available in the art.

The term "alkyl" means a straight or branched chain hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

The term "aryl" means an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthyl, indanyl, and biphenyl.

The term "Group IA metal" is also known as an alkali metal and includes, for example, lithium, sodium and potassium.

The term "Group IIA metal" is also known as an alkaline earth metal and includes, for example, calcium, barium, strontium, magnesium.

The term "pharmaceutically-acceptable" is used adjectivally in this specification to mean that the modified noun is appropriate for use as a pharmaceutical product or as a part of a pharmaceutical product.

With reference to the use of the words "comprise" or "comprises" or "comprising" in this patent (including the claims) those words are used on the basis and clear understanding that they are to be interpreted inclusively, rather than exclusively, and that Applicants intend each of those words to be so interpreted in construing this patent, including the claims below.

The following are definitions for various abbreviations used herein:
MHz is Megahertz.
Hz is Hertz.
J is Coupling Constant.
m/z is mass to charge ratio.
° C. is degrees Celsius.
g is gram.
mg is milligrams.
mmole is millimoles.
mL is milliliters.
μL is microliters.
M is molar.
HPLC is high performance liquid chromatography.
"DMAC" is N,N-dimethylacetamide.
"DMAP" is dimethylaminopyridine.
"DMF" is dimethylformamide.
"DMI" is 1,3-dimethylimidazolidinone.
"DMPU" is 1,3-dimethyl-3,4,5,6-tetrahydro-2(1H)-pyrimidinone.
"DMSO" is dimethylsulfoxide.
"ee" is enantiomer excess.
"HCl" is hydrochloric acid.
"MTBE" is methyl tert-butyl ether.
"NMP" is 1-methyl-2-pyrrolidinone.
"TEA" is triethylamine.
"TFA" is trifluoroacetic acid.
"THF" is tetrahydrofuran.

GENERIC SYNTHESIS

This invention, in part, is directed to processes for the preparation of a compound of Formula I:

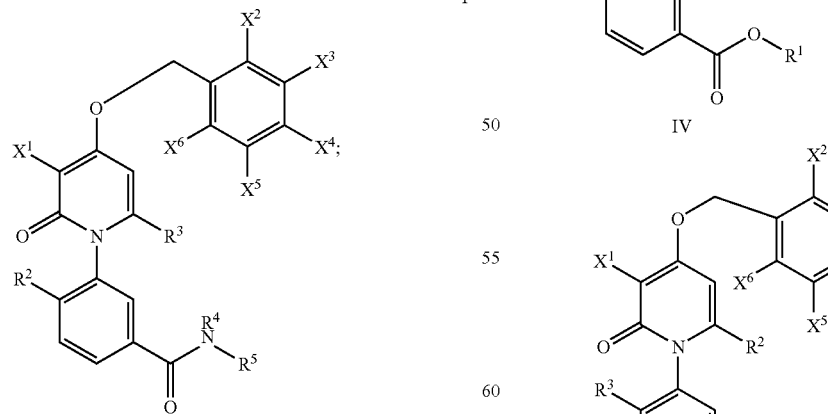

wherein $X^1$, $X^2$, $X^3$, $X^4$, $X^5$ and $X^6$ are independently H, halo or a $C_1$-$C_6$ alkyl; $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

A compound of Formula I can be made by either the following described racemic route (Route 1) or chiral route (Route 2).

The compounds described in the invention may exist as atropisomers, i.e., chiral rotational isomers. The invention encompasses the racemic and the resolved atropisomers. In some embodiments one atropisomer is preferred over the other. In the racemic route a preferred atropisomer can be separated by chiral column chromatography. In the chiral route the need for chiral column chromatography has been eliminated by utilizing a selective enzymatic hydrolysis approach.

In one embodiment, the present invention provides a process for the preparation of a racemic compound of formula I. Route 1 is generally presented in Scheme 1.

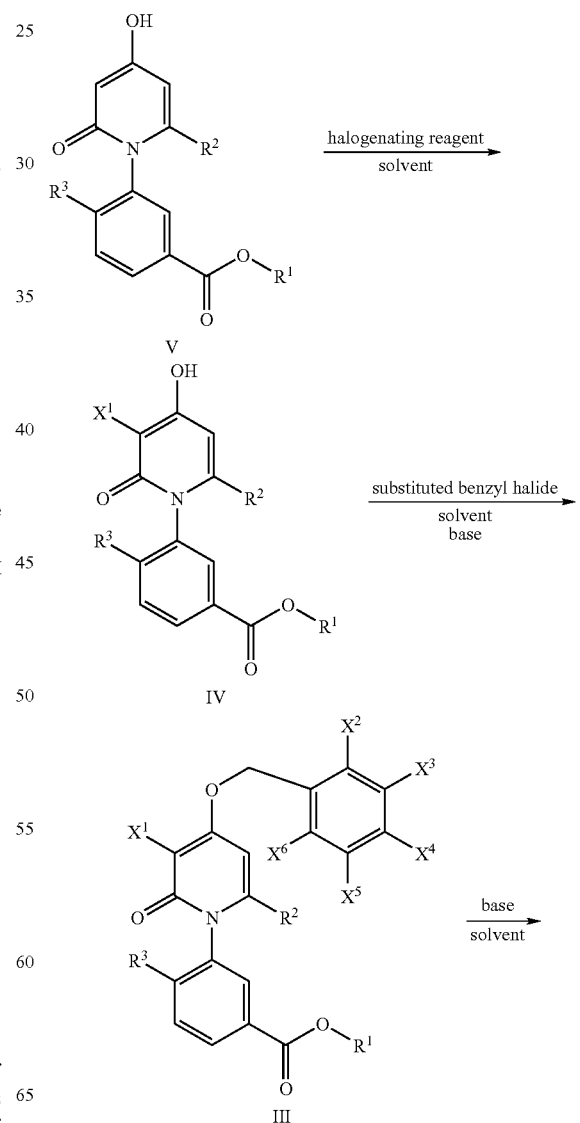

-continued

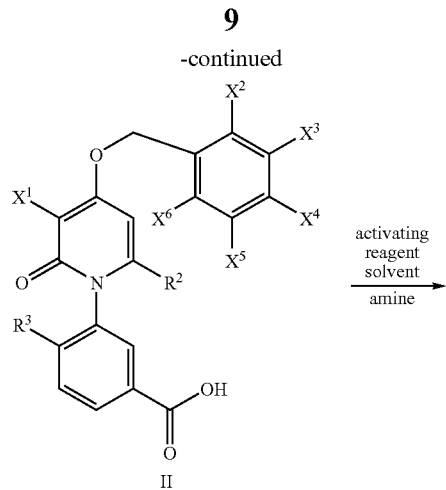

II

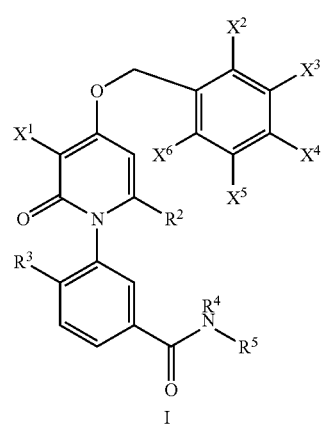

I wherein $X^1$, $X^2$, $X^3$, $X^4$, $X^5$ and $X^6$ are independently H, halo or a $C_1$-$C_6$ alkyl; $R^1$ is a $C_1$-$C_6$ alkyl or aryl; $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Preparation of a Compound of Formula V—Method 1

In one embodiment, the present invention provides a process for the preparation of a compound of formula V comprising contacting a compound of formula VI with a compound of formula VII in the presence of at least one solvent.

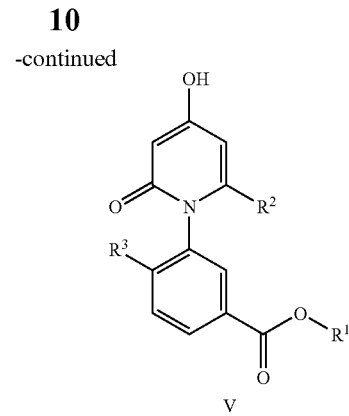

V wherein $R^1$ is a $C_1$-$C_6$ alkyl or aryl; $R^2$ is H, halo or a $C_1$-$C_6$ alkyl; and $R^3$ is halo or a $C_1$-$C_6$ alkyl.

Typically a compound of formula VI is contacted with a compound of formula VII in the presence of at least one solvent and a base.

The process is typically carried out at a temperature from about 30° C. to about 300° C. In one embodiment the temperature is from about 45° C. to about 150° C. In another embodiment the temperature is from about 60° C. to about 100° C.

The process is typically carried out for a time period from about 4 hours to about 60 hours. In one embodiment the time period is from about 2 hours to about 40 hours. In another embodiment the time period is from about 15 hours to about 25 hours.

The solvent is a polar solvent or a nonpolar solvent. Examples of useful polar solvents include ethylene glycol and trifluoroethanol. Examples of useful nonpolar solvents include dichlorobenzene, xylenes and diphenyl ether. In one embodiment the solvent is dichlorobenzene, xylenes, diphenyl ether, ethylene glycol, or trifluoroethanol. In another embodiment the solvent is trifluoroethanol or ethylene glycol. In another embodiment the solvent is ethylene glycol.

In one embodiment the base is an inorganic base or organic base. In one embodiment the base is a carbonate, bicarbonate or alkoxide of a Group IA or IIA metal, for example, potassium carbonate, potassium t-butoxide, or sodium bicarbonate. In one embodiment the base is, for example, a hindered tertiary amine such as N,N-diisopropylethylamine, triethylamine (TEA) or dimethylaminopyridine (DMAP). In one embodiment the base is potassium carbonate Preparation of a Compound of Formula V—Method 2

In one embodiment, the present invention provides a process for the preparation of a compound of formula V comprising contacting a compound of formula VII with a compound of formula VIII.

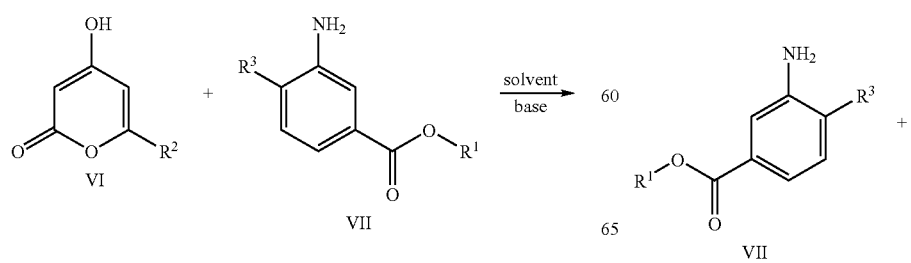

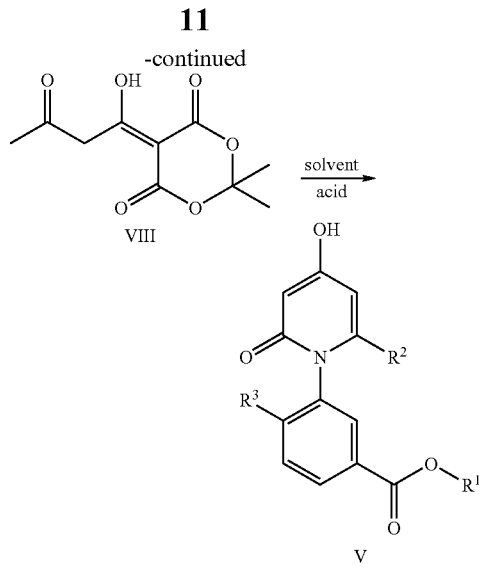

wherein $R^1$ is a $C_1$-$C_6$ alkyl or aryl; $R^2$ is H, halo or a $C_1$-$C_6$ alkyl; and $R^3$ is halo or a $C_1$-$C_6$ alkyl.

Typically a compound of formula VII is contacted with a compound of formula VIII in the presence of at least one solvent and an acid.

The process is typically carried out at a temperature from about 0° C. to about 250° C. In one embodiment the temperature is from about 5° C. to about 100° C. In another embodiment the temperature is from about 15° C. to about 60° C.

The process is typically carried out for a time period from about 0.01 hour to about 10 hours. In one embodiment the time period is from about 0.5 hour to about 7 hours. In another embodiment the time period is from about 1 hour to about 7 hours.

The solvent is a polar solvent or a nonpolar solvent. Useful examples of polar solvents include acetic acid, lower alkyl carboxylicic acid and dimethylformamide. Useful examples of nonpolar solvents include dioxane, tetrahydrofuran, methyl tert-butyl ether, diethyl ether, toluene and dichloromethane. In one embodiment the solvent is dioxane, tetrahydrofuran, methyl tert-butyl ether, diethyl ether, acetic acid or lower alkyl carboxylic acid, dichloromethane, or dimethylformamide. In one embodiment the solvent is dioxane, tetrahydrofuran, acetic acid or dichloromethane. In one embodiment the solvent is dioxane.

In one embodiment the acid is an organic acid. In another embodiment the organic acid is a lower alkyl or a substituted lower alkyl carboxylic acid, or a sulfonic acid such as p-toluenesulfonic acid, or methanesulfonic acid. In one embodiment the sulfonic acid is methanesulfonic acid.

A Compound of Formula VIII Synthesis

A process for preparing a compound of formula VIII comprising contacting Meldrum's acid with diketene in the presence of a base and at least one solvent.

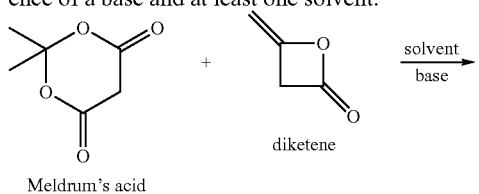

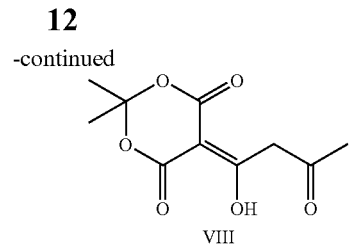

The following procedure is similar to the one reported in the literature at Kang, J; Kim, Y; Park, M; Lee, C.; Kim, W. Synthetic Communications (1984), 14(3), 265-9.

The process is typically carried out at a temperature from about 0° C. to about 100° C. In one embodiment the temperature is from about 5° C. to about 50° C. In another embodiment the temperature is from about 20° C. to about 25° C.

The process is typically carried out for a time period from about 0.01 hour to about 25 hours. In one embodiment the time period is from about 0.5 hour to about 10 hours. In another embodiment the time period is from about 1 hour to about 5 hours.

In one embodiment the base is an organic or inorganic base. Examples of useful inorganic bases include Group IA or IIA carbonates, bicarbonates or alkoxides, such as potassium carbonate, potassium t-butoxide, and sodium bicarbonate. Examples of useful organic bases include triethylamine (TEA), dimethylaminopyridine (DMAP), and N,N-diisopropylethylamine. In one embodiment the base is potassium carbonate, TEA or DMAP. In another embodiment the base is TEA.

Step 1—Halogenation

In one embodiment, the present invention provides a process for preparing a compound of formula IV comprising contacting a compound of formula V with a halogenating reagent.

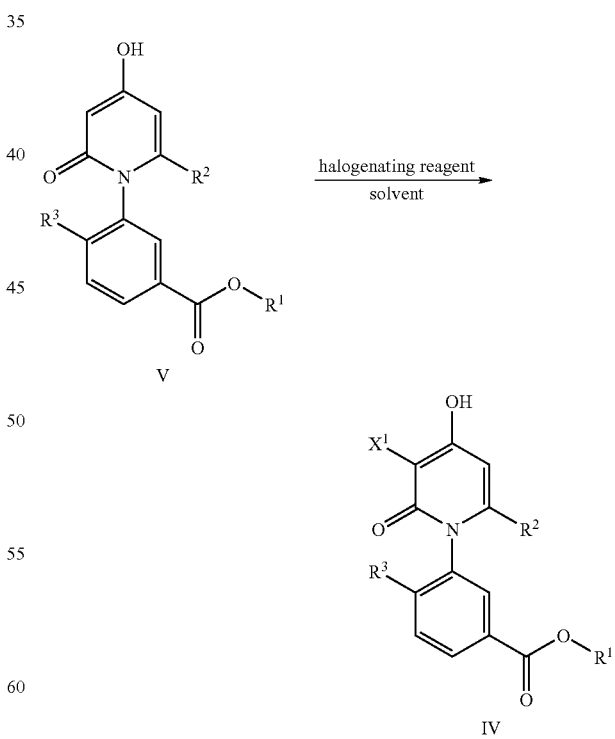

wherein $R^1$ is a $C_1$-$C_6$ alkyl or aryl; $R^2$ is H, halo or a $C_1$-$C_6$ alkyl; and $R^3$ is halo or a $C_1$-$C_6$ alkyl.

Typically a compound of formula V is contacted with a halogenating reagent in the presence of at least one solvent.

The process is typically carried out at a temperature from about −40° C. to about 50° C. In one embodiment the temperature is from about −15° C. to about 20° C. In another embodiment the temperature is from about −10° C. to about 10° C.

The process is typically carried out for a time period from about 0.5 hour to about 10 hours. In one embodiment the time period is from about 1.5 hour to about 5 hours. In one embodiment the time period is from about 1 hour to about 3 hours.

In one embodiment the solvent is a polar solvent. Useful examples include acetonitrile, acetic acid, or an acetic acid containing a co-solvent such as water or lower alkyl alcohols. In one embodiment the solvent is, for example, acetonitrile, acetic acid, or an acetic acid containing a co-solvent such as water or lower alkyl alcohols. In one embodiment the solvent is an acetic acid/water solution. In another embodiment the solvent is acetonitrile.

The halogenating reagent can be neat or a solution. In one embodiment the halogenating reagent is a brominating or a chlorinating reagent. In one embodiment the brominating or chlorinating reagent is, for example, phenyl triethylammonium tribromide, 1,3-dibromo-5,5-dimethylhydantoin, N-bromosuccinimide, pyridinium bromide, perbromide, bromine, dibromotriphenylphosphorane, bromine chloride, N-bromohydantoin, N-bromocaprolactam, N-chlorosuccinimide, sodium hypochlorite, chlorine, sulfuryl chloride, cupric bromide, phosphorus pentachloride, or t-butyl hypochlorite. In one embodiment the brominating or chlorinating reagent is 1,3-dibromo-5,5-dimethylhydantoin, bromine, bromide chloride or chlorine. In another embodiment the brominating reagent is bromine. In another embodiment the brominating reagent is 1,3-dibromo-5,5-dimethylhydantoin.

The halogenation may be conducted in the presence of an acid. In one embodiment the acid is an organic or inorganic acid. Examples of useful acids include tetrafluoroboric acid, hydrobromic acid, hydrochloric acid, hydrofluoric acid, sulfuric acid and phosphoric acid. In one embodiment the acid is tetrafluoroboric acid.

Step 2—Benzylation

In one embodiment, the present invention provides a process for preparing a compound of formula III comprising contacting a compound of formula IV with a substituted benzyl halide.

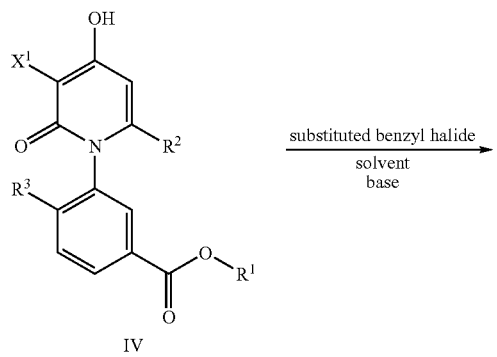

-continued

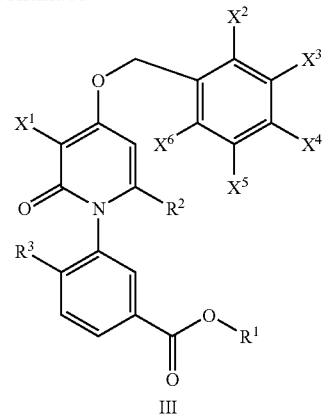

wherein $X^1$, $X^2$, $X^3$, $X^4$, $X^5$ and $X^6$ are independently H, halo or a $C_1$-$C_6$ alkyl; $R^1$ is a $C_1$-$C_6$ alkyl or aryl; $R^2$ is H, halo or a $C_1$-$C_6$ alkyl; and $R^3$ is halo or a $C_1$-$C_6$ alkyl.

Typically a compound of formula IV is contacted with a substituted benzylhalide in the presence of at least one solvent and a base.

The process is typically carried out at a temperature from about 0° C. to about 200° C. In one embodiment the temperature is from about 15° C. to about 100° C. In another embodiment the temperature is from about 25° C. to about 75° C.

The process is typically carried out for a time period from about 0.5 hour to about 40 hours. In one embodiment the time period is from about 1 hour to about 10 hours. In another embodiment the time period is from about 1 hour to about 5 hours.

In one embodiment the substituted benzylhalide is:

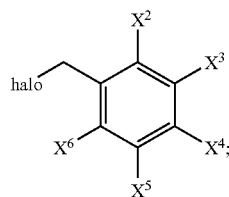

wherein halo is chloride, bromide or iodide; and $X^2$, $X^3$, $X^4$, $X^5$ and $X^6$ are independently H, halo, or a $C_1$-$C_6$ alkyl. In one embodiment the halo-substituted benzylhalide is, for example, 2,4-difluorobenzylbromide, 2,3-difluorobenzylbromide, 2,5-difluorobenzylbromide, 2,4-difluorobenzylchloride, 2,3-difluorobenzylchloride or 2,5-difluorobenzylchloride. In another embodiment the halo-substituted benzylchloride is 2,4-difluorobenzylchloride. In another embodiment the halo substituted benzyl halide is 2,4-difluorobenzylbromide.

In one embodiment the solvent is a polar aprotic solvent. In one embodiment the polar aprotic solvent is, for example, N,N-dimethylformamide (DMF), N,N-dimethylacetamide (DMAC), N-methylpyrrolidinone (NMP), 1,3-dimethylimidazolidinone (DMI) or 1,3-dimethyl-3,4,5,6-tetrahydro-2 (1H)-pyrimidinone (DMPU). In another embodiment the polar aprotic solvent is N,N-dimethylformamide. In another embodiment the solvent is N-methylpyrrolidinone.

In one embodiment the base is an organic or inorganic base. Examples of useful inorganic bases include Group IA or IIA carbonates, bicarbonates or alkoxides, such as potassium carbonate, potassium t-butoxide, and sodium bicarbonate. Examples of useful organic bases include triethylamine (TEA), dimethylaminopyridine (DMAP), and N,N-diisopropylethylamine. In one embodiment the base is potassium carbonate, potassium t-butoxide or sodium bicarbonate. In another embodiment the base is potassium carbonate.

Step 3—Hydrolysis

In one embodiment, the present invention provides a process for preparing a compound of formula II comprising contacting a compound of formula III with a base.

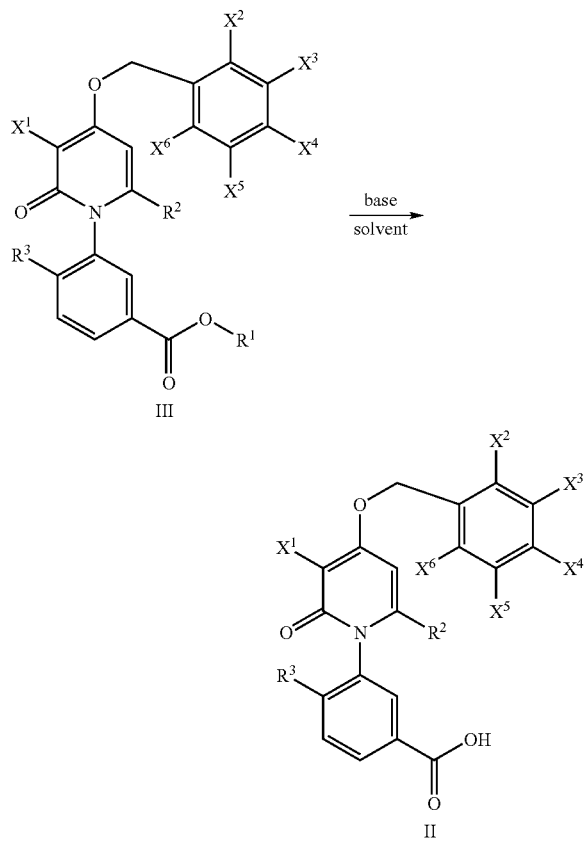

wherein $X^1$, $X^2$, $X^3$, $X^4$, $X^5$ and $X^6$ are independently H, halo or a $C_1$-$C_6$ alkyl; $R^1$ is a $C_1$-$C_6$ alkyl or aryl; $R^2$ is H, halo or a $C_1$-$C_6$ alkyl; and $R^3$ is halo or a $C_1$-$C_6$ alkyl.

Typically a compound of formula III is contacted with a base in the presence of at least one solvent.

The process is typically carried out at a temperature from about 10° C. to about 100° C. In one embodiment the temperature is from about 20° C. to about 80° C. In another embodiment the temperature is from about 40° C. to about 75° C.

The process is typically carried out for a time period from about 0.5 hour to about 40 hours. In one embodiment the time period is from about 1 hour to 10 hours. In another embodiment the time period is from about 1 hour to about 5 hours.

In one embodiment the base is an inorganic base. Useful examples of inorganic bases include a group IA or IIA hydroxide base or carbonate base such as potassium, lithium, cesium and sodium hydroxide. In one embodiment the base is potassium, lithium, cesium or sodium hydroxide. In one embodiment the base is sodium hydroxide.

In one embodiment the solvent is one solvent. In another embodiment the solvent comprises a mixture of two or more solvents. In one embodiment the solvent is, for example, water with or without a water miscible organic co-solvent such as lower alkyl alcohols, tetrahydrofuran (THF), acetone, acetonitrile, N,N-dimethylformamide or dimethylsulfoxide (DMSO). In one embodiment the solvent is water. In one embodiment the solvent comprises acetonitrile and water.

In another embodiment the compound of formula III can be hydrolyzed with a proteolytic enzyme or a nucleophile in a non-aqueous condition.

Step 4—Amidation

In one embodiment, the present invention provides a process for preparing a compound of formula I that comprising reacting a compound of formula II with an appropriate activating agent, and then contacting the resulting mixture with an appropriate primary or secondary amine to produce a compound of formula I.

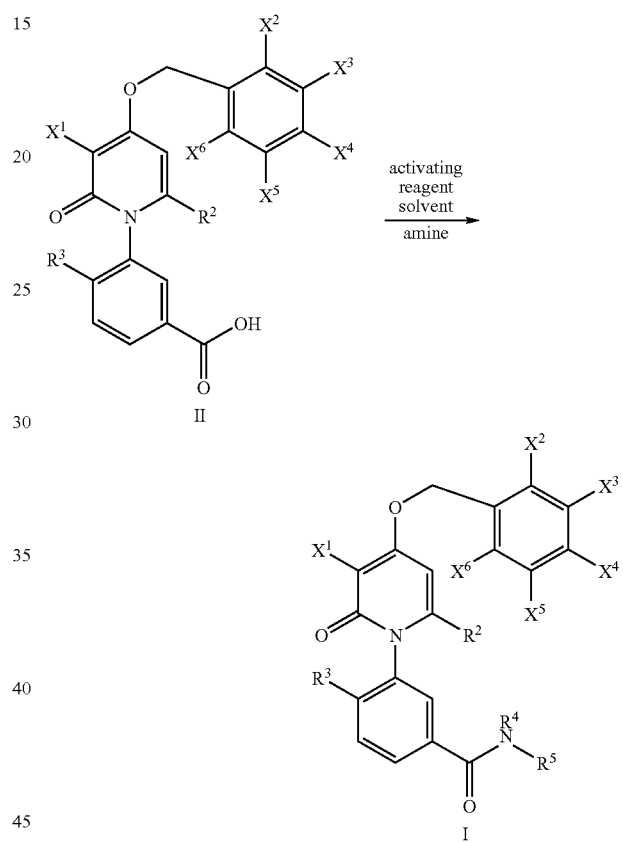

wherein $X^1$, $X^2$, $X^3$, $X^4$, $X^5$ and $X^6$ are independently H, halo or a $C_1$-$C_6$ alkyl; $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Typically a compound of formula II is contacted with an activating agent in the presence of at least one solvent and then the resulting mixture is contacted with an amine.

The process is typically carried out at a temperature from about 0° C. to about 50° C. In one embodiment the temperature is from about 1° C. to about 25° C. In another embodiment the temperature is from about 5° C. to about 15° C.

The process is typically carried out for a time period from about 0.01 hour to about 35 hours. In one embodiment the time period is from about 0.5 hour to about 10 hours. In another embodiment the time period is from about 1 to about 5 hours.

An activating agent is a reagent that activates the carboxylic acid. Activating means increasing the electrophilicity of the carboxylic acid thereby increasing its reactivity toward nucleophilic attack. In one embodiment the activating agent is carbonyldiimidazole, dicyclohexylcarbodiimide, thionyl chloride, oxalyl chloride, phosphorus oxychloride, phosphorus trichloride, phosphorus pentachloride, phenyl triethylammonium tribromide, pyridinium bromide, perbromide, bromine, dibromotriphenylphosphorane, bromine chloride, N-bromohydantoin or N-bromocaprolactam. In one embodiment the activating agent is carbonyldiimidazole, dicyclohexylcarbodiimide, thionyl chloride, oxalyl chloride, phosphorus oxychloride, phosphorus trichloride or phosphorus pentachloride. In one embodiment the activating reagent is oxalyl chloride. In another embodiment the activating reagent is carbonyldiimidazole.

The solvent is a polar solvent or a nonpolar solvent. Useful examples of polar solvents include dimethylformamide, acetic acid and lower alkyl carboxylic acid. Examples of useful nonpolar solvents include dichloroethane, tetrahydrofuran, dioxane, methyl tert-butyl ether, diethylether and toluene. In one embodiment the solvent is, for example, dimethylformamide, dichloroethane, tetrahydrofuran, dioxane, methyl tert-butyl ether, or toluene. In one embodiment the solvent is dimethylformamide, dichloroethane, tetrahydrofuran or dioxane. In another embodiment the solvent is dichloroethane. In one embodiment the solvent is dimethylformamide.

In one embodiment the amine is $HNR^4R^5$ wherein $R^4$ is H or a $C_1$-$C_6$ alkyl; and $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen. In one embodiment $R^4$ is H. In one embodiment $R^5$ is a $C_1$-$C_6$ alkyl. In one embodiment, the amine is methylamine. Typically the amine is combined with a solvent prior to addition. In one embodiment the solvent is methanol, ethanol, tetrahydrofuran or water. In another embodiment the solvent is methanol, tetrahydrofuran or water. In one embodiment the solvent is tetrahydrofuran. In one embodiment the amine is a solution of methyl amine in tetrahydrofuran.

Optionally an acid can be used to work up the reaction. In one embodiment the acid is an organic or inorganic acid. Examples of useful acids include acetic acid, citric acid, HCl and sulfuric acid. In one embodiment the acid is acetic acid, citric acid, HCl, or sulfuric acid. In one embodiment the acid is HCl, acetic acid or sulfuric acid. In one embodiment the acid is HCl.

Compounds of formula I can be isolated by filtration or standard extractive or evaporative methods.

Those skilled in the art can appreciate an alternative to making this product using a mixed anhydride intermediate such as a lower alkyl carboxylic acid anhydride intermediate or acyl imidazole intermediate in place of the acid chloride intermediate. A mixed anhydride intermediate can be synthesized using a typical alkyl chloroformate in the presence of a typical hindered amine base. The acyl imidazole intermediate can be synthesized using a reagent such as carbonyl diimidazole.

The sequence of steps may be rearranged in several possible ways. In one embodiment, the hydrolysis and amidation could be conducted prior to the benzylation step.

In another embodiment, the present invention provides a process for the preparation of an enantiomerically enriched mixture or exclusively a single enantiomer of a compound of formula I following Route 2. Route 2 is generally presented in Scheme 2.

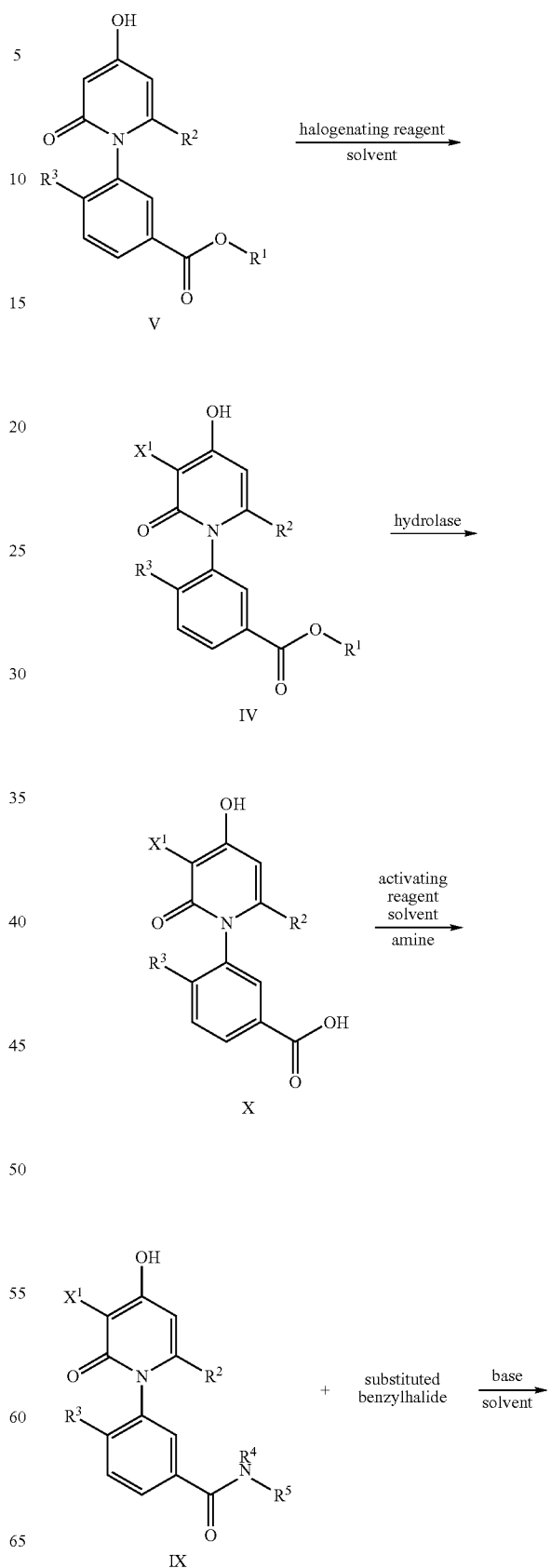

-continued

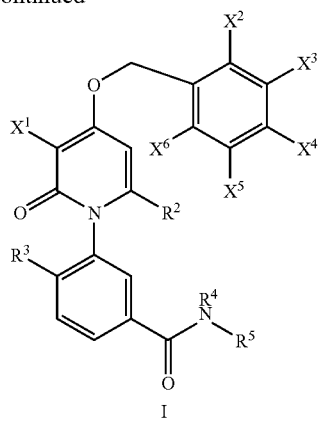

I wherein $X^1$, $X^2$, $X^3$, $X^4$, $X^5$ and $X^6$ are independently H, halo or a $C_1$-$C_6$ alkyl; $R^1$ is a $C_1$-$C_6$ alkyl or aryl; $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Compounds of Formula V and IV can be prepared as previously described in Route 1.

Step 1-Protease Reaction

In one embodiment, the present invention provides a process for preparing a compound of formula X comprising contacting a compound of formula IV with a hydrolase.

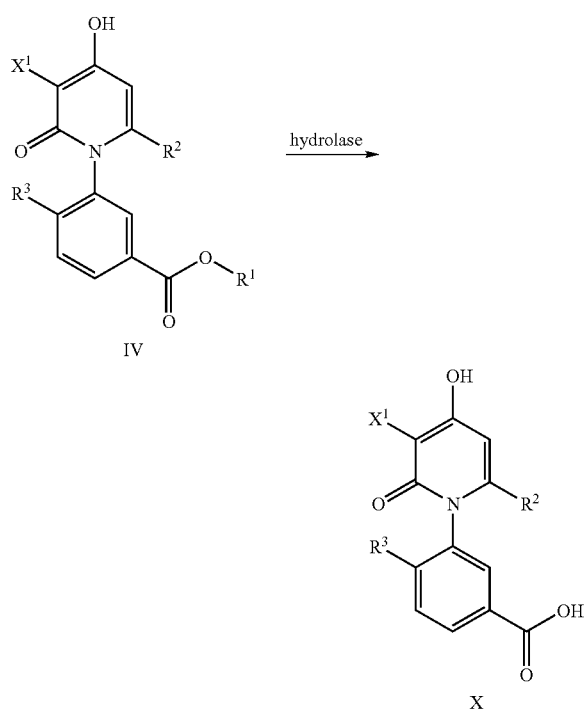

wherein $R^1$ is a $C_1$-$C_6$ alkyl or aryl, $R^2$ is H, halo or a $C_1$-$C_6$ alkyl and $R^3$ is halo or a $C_1$-$C_6$ alkyl.

Typically a compound of formula IV is contacted with hydrolase in the presence of a buffer solution.

The process is typically carried out at a temperature from about 5° C. to about 80° C. In one embodiment the temperature is from about 10° C. to about 60° C. In another embodiment the temperature is from about 20° C. to about 40° C.

The process is typically carried out for a time period from about 5 hours to about 100 hours. In one embodiment the time period is from about 25 hours to about 75 hours. In another embodiment the time period is from about 30 hours to about 60 hours.

The process is typically carried out at a pH of about 6 to about 12. In one embodiment the pH is from about 8 to about 11. In another embodiment the pH is from about 9 to about 10. In another embodiment the pH is about 9.

In one embodiment the buffer solution is an inorganic buffer solution. In another embodiment the buffer solution is, for example, potassium phosphate buffer solution or an inorganic bicarbonate buffer. In one embodiment the buffer solution is dibasic potassium phosphate buffer solution. Typically the molarity of the buffer solution is about 1 M.

In one embodiment the appropriate enzymatic solution is a hydrolase such as lipase or protease. In one embodiment the hydrolase produces the (−) enantiomer of a compound of Formula X in excess. In one embodiment particularly useful hydrolases are those that produce the (−) enantiomer in at least 80% enantiomeric excess. In another embodiment particularly useful hydrolases are those that produce the (−) enantiomer in at least 85% enantiomeric excess. In another embodiment particularly useful hydrolases are those that produce the (−) enantiomer in at least 90% enantiomeric excess. In another embodiment particularly useful hydrolases are those that produce the (−) enantiomer in at least 95% enantiomeric excess. In another embodiment particularly useful hydrolases are those that produce the (−) enantiomer in at least 99% enantiomeric excess. In one embodiment the hydrolase is *Bacillus* sp. protease solution (Savinase®, Novozyme, Bagsvaerd, Denmark).

In one embodiment the hydrolase produces a compound of Formula X as a racemic mixture. In another embodiment the hydrolase produces the (+) enantiomer of a compound of Formula X in excess.

In one embodiment the (−) enantiomer of a compound of formula X is preferred. The (+) enantiomer of a compound of formula IV can be isolated and removed. The (+) enantiomer can be recycled by thermal isomerization to the racemic mixture in a typical aprotic organic solvent at a temperature in a range from about 100° C. to about 300° C.

Typically the (+) enantiomer of a compound of formula IV is contacted with a high boiling aprotic solvent, halogenated or substituted aromatic or aliphatic solvent.

The high boiling aprotic solvent, halogenated or substituted aromatic or aliphatic solvent can be chlorobenzene, anisole, dioxane, NMP, N,N-dimethylformamide, or dimethylsulfoxide.

The process is typically carried out at a temperature from about 0° C. to about 200° C. In one embodiment the temperature is from about 75° C. to about 150° C. In another embodiment the temperature is from about 100° C. to about 140° C.

The process is typically carried out for a time period from about 30 hours to about 200 hours. In one embodiment the time period is from about 20 hours to about 100 hours. In another embodiment the time period is from about 50 hours to about 75 hours.

Step 3—Amidation

In one embodiment, the present invention provides a process for preparing a compound of formula IX comprising reacting a compound of formula X with an appropriate activating agent, and then contacting the resulting mixture with an appropriate primary or secondary amine to produce a compound of formula IX.

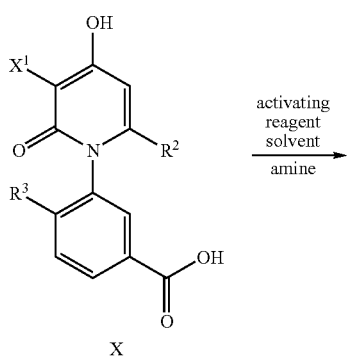

X

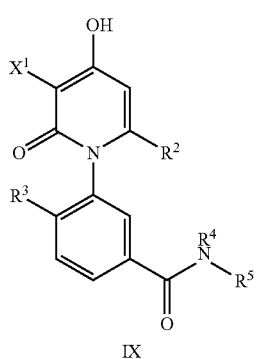

IX wherein $X^1$ is H, halo or a $C_1$-$C_6$ alkyl; $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

In one embodiment compound of Formula X and IX are the (–) enantiomers.

Typically a compound of formula X is contacted with an activating reagent in the presence of at least one solvent and then the resulting mixture is contacted with an amine.

The process is typically carried out at a temperature from about 0° C. to about 100° C. In one embodiment the temperature is from about 10° C. to about 50° C. In one embodiment the temperature is from about 15° C. to about 30° C.

The process is typically carried out for a time period from about 0.1 hour to about 10 hours. In one embodiment the time period is from about 0.5 hour to about 5 hours. In another embodiment the time period is from about 1 hour to about 3 hours.

In one embodiment the activating reagent is carbonyldiimidazole, dicyclohexylcarbodiimide, thionyl chloride, oxalyl chloride, phosphorus oxychloride, phosphorus trichloride, phosphorus pentachloride, phenyl triethylammonium tribromide, pyridinium bromide, perbromide, bromine, dibromotriphenylphosphorane, bromine chloride, N-bromohydantoin or N-bromocaprolactam. In one embodiment the activating reagent is carbonyldiimidazole, dicyclohexylcarbodiimide, thionyl chloride, oxalyl chloride, phosphorus oxychloride, phosphorus trichloride or phosphorus pentachloride. In one embodiment the reagent is oxalyl chloride. In another embodiment the activating reagent is carbonyldiimidazole.

The solvent is a polar solvent or a nonpolar solvent. Useful examples of polar solvents include dimethylformamide, acetic acid and lower alkyl carboxylic acid. Examples of useful nonpolar solvents include dichloroethane, tetrahydrofuran, dioxane, methyl tert-butyl ether, diethylether and toluene. In one embodiment the solvent is, for example, dimethylformamide, dichloroethane, tetrahydrofuran, dioxane, methyl tert-butyl ether, or toluene. In one embodiment the solvent is dimethylformamide, dichloroethane, tetrahydrofuran or dioxane. In another embodiment the solvent is dichloroethane. In one embodiment the solvent is dimethylformamide.

In one embodiment the amine is $HNR^4R^5$ wherein $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen. In one embodiment $R^4$ is H. In one embodiment $R^5$ is a $C_1$-$C_6$ alkyl. In one embodiment, the amine is methylamine. Typically the amine is combined with a solvent prior to addition. In one embodiment the solvent is methanol, ethanol, tetrahydrofuran or water. In another embodiment the solvent is methanol, tetrahydrofuran or water. In one embodiment the solvent is tetrahydrofuran. In one embodiment the amine is a solution of methyl amine in tetrahydrofuran.

Optionally an acid can be used to work up the reaction. In one embodiment the acid is an organic or inorganic acid. Examples of useful acids include acetic acid, citric acid, HCl and sulfuric acid. In one embodiment the acid is acetic acid, citric acid, HCl, or sulfuric acid. In one embodiment the acid is HCl, acetic acid or sulfuric acid. In one embodiment the acid is HCl.

Step 4—Benzylation

In one embodiment, the present invention provides a process for the preparation of a compound of formula I comprising reacting a compound of formula IX with a substituted benzylhalide.

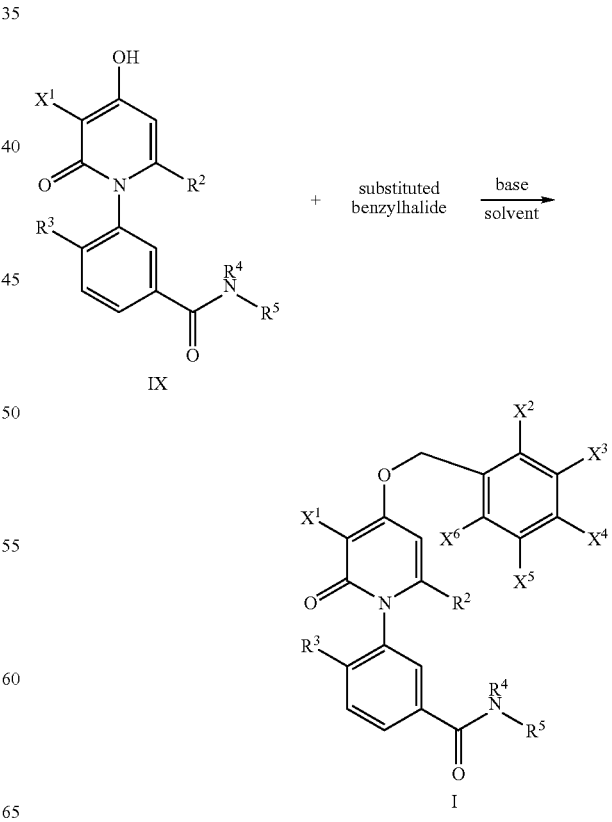

wherein $X^1$, $X^2$, $X^3$, $X^4$, $X^5$ and $X^6$ are independently H, halo or a $C_1$-$C_6$ alkyl $R^2$ is H, halo or a $C_1$-$C_6$ alkyl; $R^3$ is halo or a $C_1$-$C_6$ alkyl; and $R^4$ is H or a $C_1$-$C_6$ alkyl; $R^5$ is H, a $C_1$-$C_6$ alkyl or aryl; or $R^4$, $R^5$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

In one embodiment compound of Formula IX and I are the (−) enantiomers.

Typically a compound of formula IX is contacted with a substituted benzylhalide in the presence of a base and at least one solvent.

The process is typically carried out at a temperature from about 0° C. to about 200° C. In one embodiment the temperature is from about 25° C. to about 100° C. In another embodiment the temperature is from about 50° C. to about 75° C.

The process is typically carried out for a time period from about 0.5 hour to about 20 hours. In one embodiment the time period is from about 1 hour to about 10 hours. In another embodiment the time period is from about 2 hours to about 4 hours.

In one embodiment the substituted benzylhalide is:

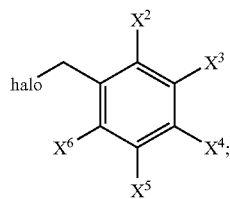

wherein halo is chloride, bromide or iodide; and $X^2$, $X^3$, $X^4$, $X^5$ and $X^6$ are independently H, halo, or a $C_1$-$C_6$ alkyl. In one embodiment the halo-substituted benzylhalide is, for example, 2,4-difluorobenzylbromide, 2,3-difluorobenzylbromide, 2,5-difluorobenzylbromide, 2,4-difluorobenzylchloride, 2,3-difluorobenzylchloride or 2,5-difluorobenzylchloride. In another embodiment the halo-substituted benzylchloride is 2,4-difluorobenzylchloride. In another embodiment the halo substituted benzyl halide is 2,4-difluorobenzylbromide.

In one embodiment the base is an organic or inorganic base. Examples of useful inorganic bases include Group IA or IIA carbonates, bicarbonates or alkoxides, such as potassium carbonate, potassium t-butoxide, and sodium bicarbonate. Examples of useful organic bases include triethylamine (TEA) or dimethylaminopyridine (DMAP); and a hindered amine such as N,N-diisopropylethylamine. In one embodiment the base is potassium carbonate, potassium t-butoxide or sodium bicarbonate. In another embodiment the base is potassium carbonate.

In one embodiment the solvent is a polar aprotic solvent. In one embodiment the polar aprotic solvent is, for example, N,N-dimethylformamide (N,N-dimethylformamide), N,N-dimethylacetamide (DMAC) or N-methylpyrrolidinone (NMP), 1,3-dimethylimidazolidinone (DMI), 1,3-dimethyl-3,4,5,6-tetrahydro-2(1H)-pyrimidinone (DMPU). In another embodiment the polar aprotic solvent is N,N-dimethylformamide. In another embodiment the solvent is N-methylpyrrolidinone.

In one embodiment the product is purified by trituration or precipitation using an appropriate solvent and/or co-solvent system. In one embodiment the solvent is methanol, 1-butanol, ethanol, ethyl acetate or 2-propanol. In one embodiment the solvent is methanol, ethanol or ethyl acetate. In one embodiment the solvent is methanol.

Those of skill in the art will appreciate that the sequence of steps may occur in alternative orders. Scheme 6 depicts some possible sequences.

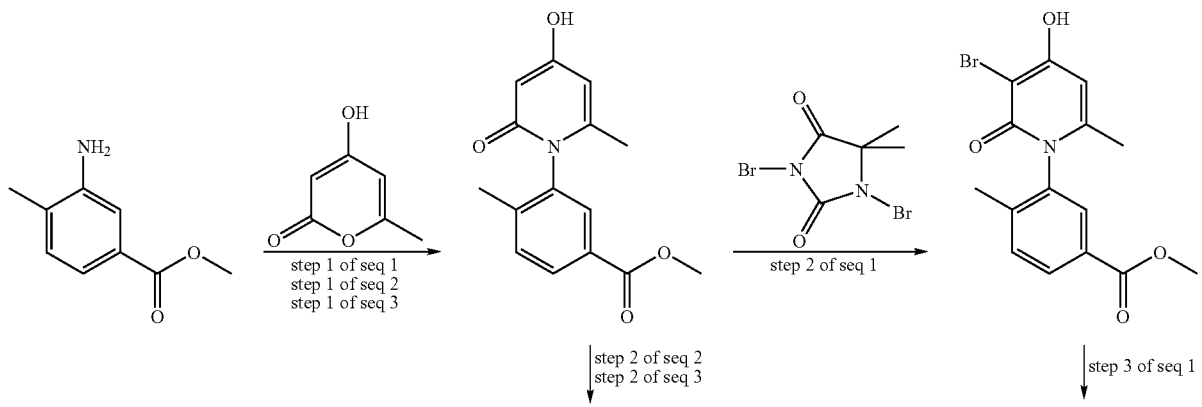

Scheme 6

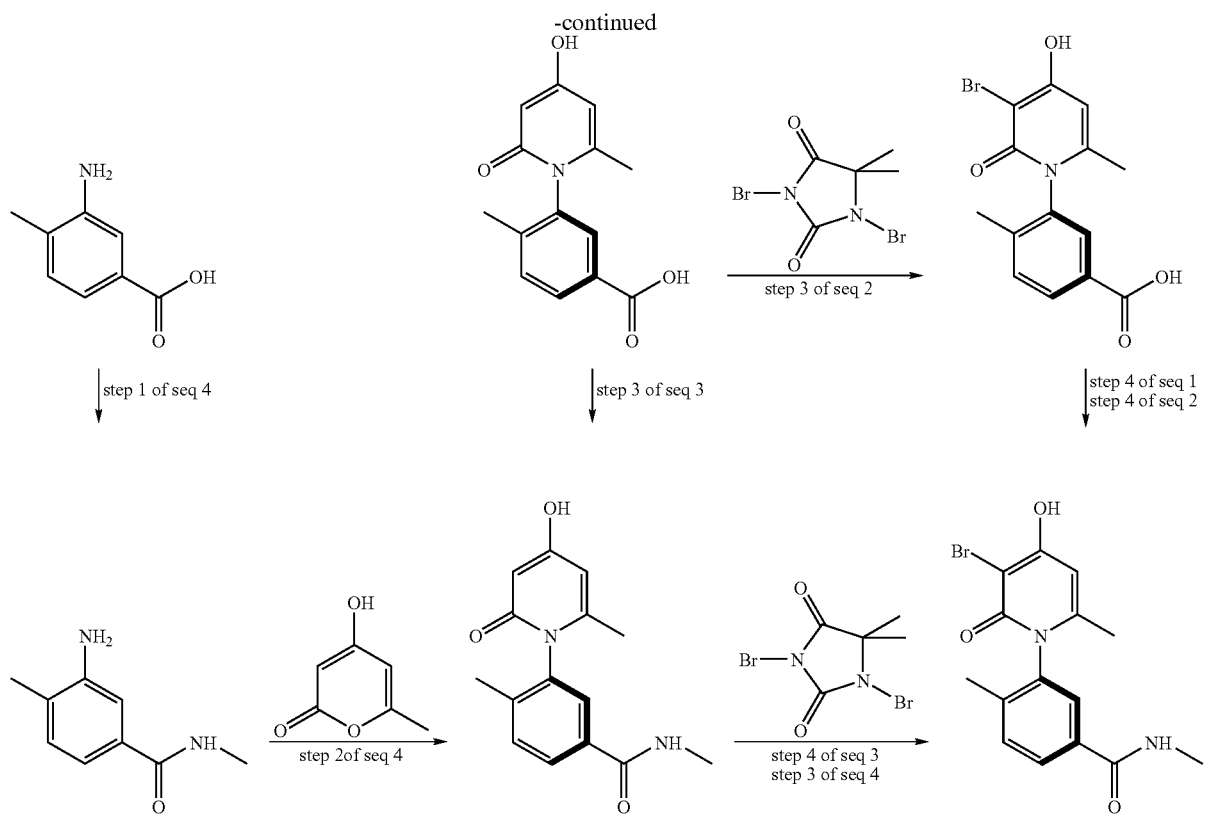

Sequence 1: halogenation, hydrolysis, amidation. Sequence 2: hydrolysis, halogenation, amidation. Sequence 3: hydrolysis, amidation, halogenation. Sequence 4: start with 3-amino-4-methyl benzoic acid, amidation, halogenation. Note that the final step in all these approaches is the benzylation step.

In one embodiment, the present invention provides novel intermediates. In one embodiment the compound is selected from methyl 3-(3-bromo-4-hydroxy-6-methyl-2-oxopyridin-1(2H)-yl)-4-methylbenzoate;

(+)-methyl 3-(3-bromo-4-hydroxy-6-methyl-2-oxopyridin-1(2H)-yl)-4-methylbenzoate;

3-(3-bromo-4-hydroxy-6-methyl-2-oxopyridin-1(2H)-yl)-N,4-dimethylbenzamide;

3-(3-bromo-4-hydroxy-6-methyl-2-oxopyridin-1(2H)-yl)-4-methylbenzoic acid;

(−)-3-(3-bromo-4-hydroxy-6-methyl-2-oxopyridin-1(2H)-yl)-4-methylbenzoic acid; and (−)-1-(5-(1H-imidazole-1-carbonyl)-2-methyl phenyl)-3-bromo-4-hydroxy-6-methylpyridin-2(1H)-one;

or a pharmaceutically acceptable salt thereof.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The compounds described in the invention may exist as atropisomers, i.e., chiral rotational isomers. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; thermal or kinetic resolution; or derivatizing the racemic mixture with a resolving reagent to generate diastereomers, separating the diastereomers via chromatography or selective crystallization, and removing the resolving agent to generate the original compound in enantiomerically enriched form. Any of the above procedures can be repeated or combined to increase the enantiomeric purity of a compound.

The compounds described in the invention may exist as atropisomers, i.e., chiral rotational isomers. The invention encompasses the racemic and the resolved atropisomers. The following illustration generically shows a compound (Z) that can exist as atropisomers as well as its two possible atropisomers (A) and (B). This illustration also shows each of atropisomers (A) and (B) in a Fischer projection. In this illustration, $R^3$ and $X^1$ carry the same definitions as set forth for Formula I, $R_{p'}$ is a substituent within the definition of $R^2$, $R_p$ is a substituent within the definition of $CONR^4R^5$, and D represents the substituted benzyloxy.

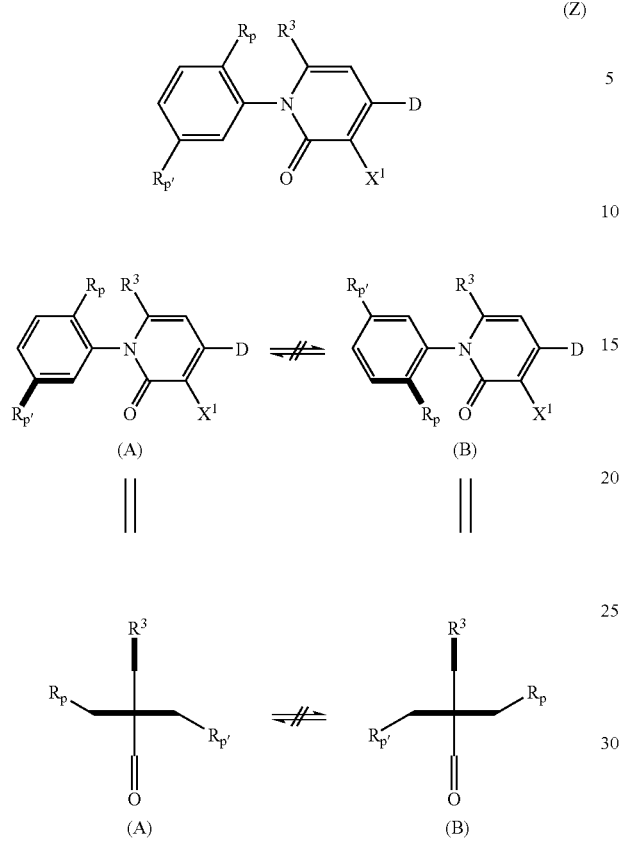

When enantiomerically enriched, one enantiomer is present in greater amounts that the other and the extent of enrichment can be defined by an expression of enantiomer excess ("ee"), which is defined as 100 (2x−1) wherein x is the mole fraction of the dominant enantiomer in the enantiomer mixture (e.g., an ee of 20% corresponds to a 60:40 ratio of enantiomers).

DETAILED EXAMPLES

The following examples are merely illustrative, and not limiting to the remainder of this disclosure in any way.

Example 1

Schemes 7 and 8 depict the overall syntheses that are described in Example 1.

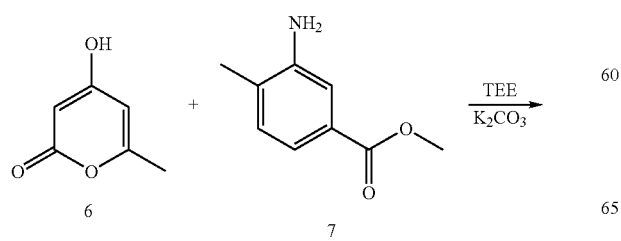

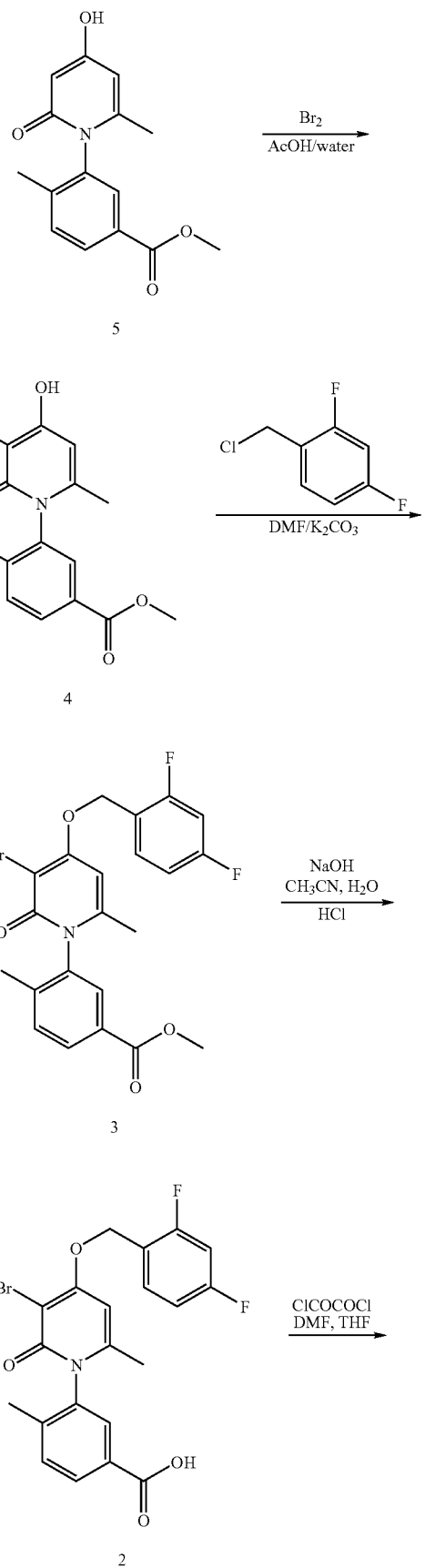

29
-continued
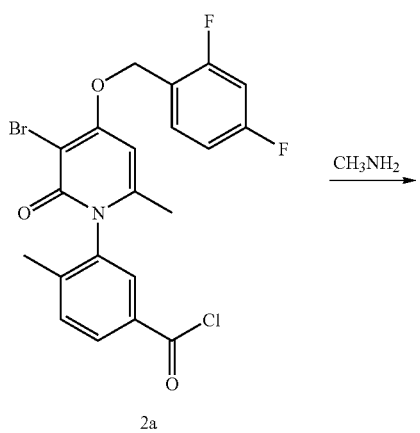
2a
→ CH₃NH₂
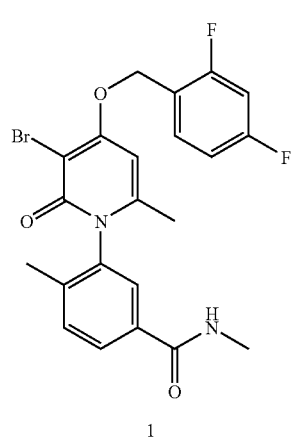
1
Scheme 8
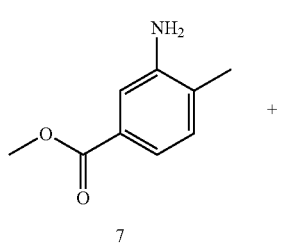
7
+
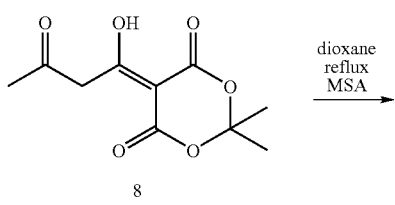
8
→ dioxane reflux MSA
30
-continued
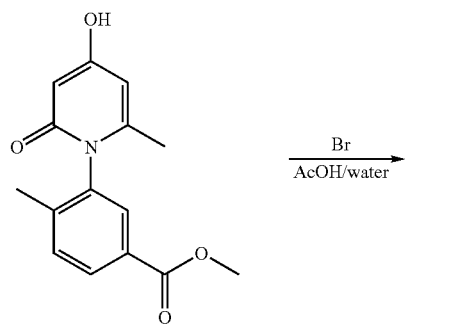
5
→ Br AcOH/water
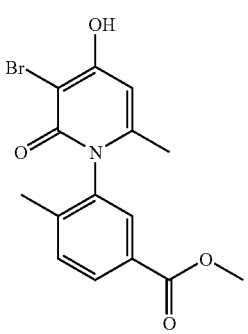
4
→ 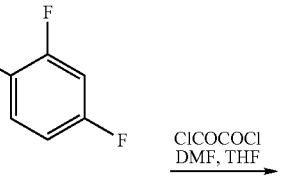 DMF/K₂CO₃
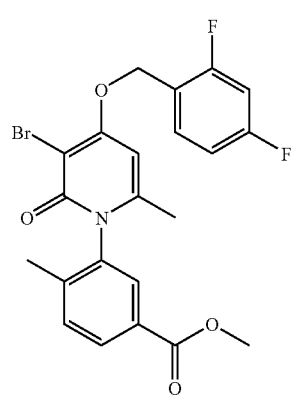
3
→ NaOH CH₃CN, H₂O HCl
2
→ ClCOCOCl DMF, THF -continued

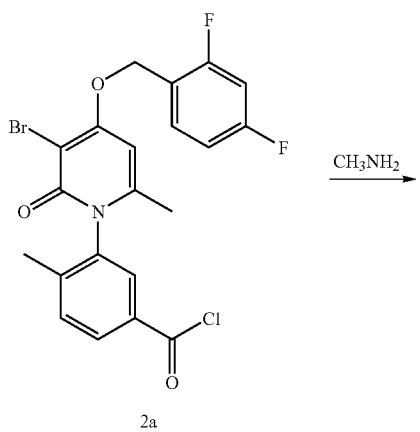

2a

↓ CH₃NH₂

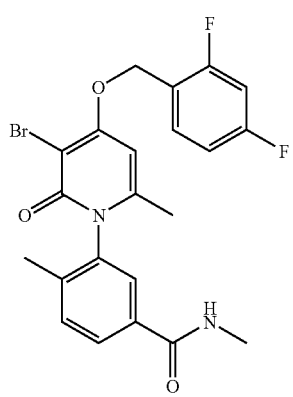

1

The racemic process to prepare (−)-3-[3-bromo-4-[(2,4-difluorobenzyl)oxy]-6-methyl-2-oxopyridin-1(2H)-yl]-N,4-dimethylbenzamide (1) is described as follows:

Synthesis of methyl 3-(4-hydroxy-6-methyl-2-oxopyridin-1(2H)-yl)-4-methylbenzoate (5) Using Pyrone 6

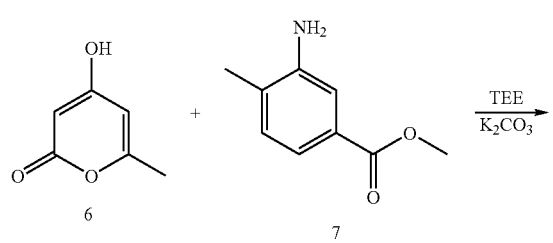

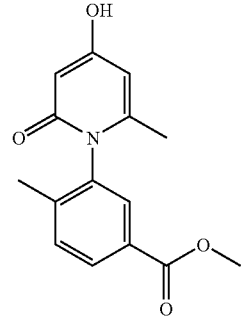

5

4-hydroxy-6-methylpyranone (6) (1.18 kg, 9.34 moles), methyl-3-amino-4-methyl benzoate (7) (1.0 kg. 6.21 moles), catalytic K₂CO₃ (102 gm, 0.74 moles) and 2 L of trifluoroethanol were mixed and heated to 80-87° C., under nitrogen for 22 hours. After the completion of reaction, the mixture was cooled to 65° C. and 11.3 L ethyl acetate was added and the solution gradually cooled to 5-10° C. A product was collected, washed with 2 L ethyl acetate to give about 55% isolated yield of methyl 3-(4-hydroxy-6-methyl-2-oxopyridin-1(2H)-yl)-4-methylbenzoate.

Alternatively methyl 3-(4-hydroxy-6-methyl-2-oxopyridin-1(2H)-yl)-4-methylbenzoate (5) can be prepared using 5-(1-hydroxy-3-oxobutylidene)-2,2-dimethyl-1,3-dioxane-4,6-dione (8) as follows:

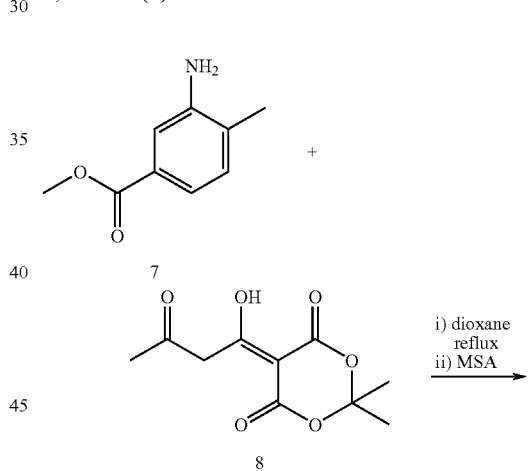

A mixture of methyl 3-amino-4-methylbenzoate (7) (2.0 g, 12.1 mmoles) and 5-(1-hydroxy-3-oxobutylidene)-2,2-dimethyl-1,3-dioxane-4,6-dione (8) (3.86 g, 16.94 mmol, 1.4 eq.) in dioxane (20 mL) was heated at reflux for 5 minutes and cooled to 50° C. The mixture was then treated with 1.16 g of methane-sulfonic acid and heated at reflux for five minutes. Liquid chromatography indicated the reaction (cyclization) was essentially complete. The mixture was poured in 60 mL of crushed ice-water and stirred for 1.5 hours. The precipitate was filtered, washed with water and air dried to give 2.47 g (75% yield) of the product.

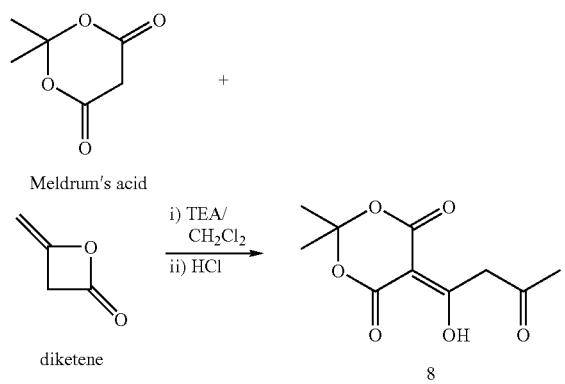

Meldrum's acid diketene

The above procedure is a modification of the procedure described in the literature at Kang, J; Kim, Y; Park, M; Lee, C.; Kim, W. Synthetic Communications (1984), 14(3), 265-9. In essence Meldrum's acid was reacted with diketene in dichloromethane in the presence of TEA at 20-25° C. for 2 hours to give 80% of 5-(1-hydroxy-3-oxobutylidene)-2,2-dimethyl-1,3-dioxane-4,6-dione (8).

Synthesis of methyl 3-(3-bromo-4-hydroxy-6-methyl-2-oxopyridin-1(2H)-yl)-4-methylbenzoate (4)

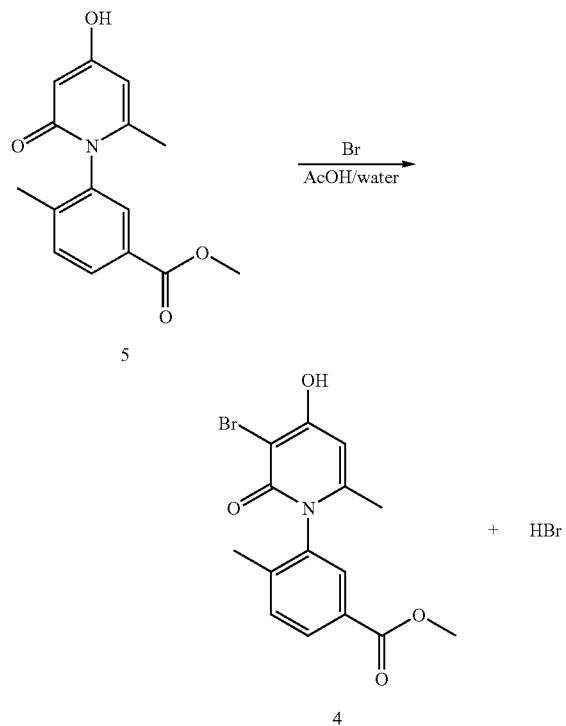

A suspension of methyl 3-(4-hydroxy-6-methyl-2-oxopyridin-1(2H)-yl)-4-methylbenzoate (5) (1.6 kg, 5.85 moles) in 6.4 L acetic acid/1.6 L water and cooled to 15° C. A solution of 973 g bromine in 1.6 L acetic acid was prepared and added slowly to the reaction via dropping funnel. During the addition of bromine, the mixture became homogeneous followed by the formation of a white precipitate. After the addition was completed, the mixture was stirred for another 15 minutes. The mixture was diluted with 16 L water; and the product was filtered and washed with 12 L water followed by 9.6 L cold acetonitrile (0-5° C.). The solid was dried to yield 1.85 kg (90%) product. $^1$H NMR (300 MHz, DMSO-$d_6$) δ 1.80 (s, 3H), 2.04 (s, 3H), 3.86 (s, 3H), 6.15 (s, 1H), 7.59 (d, J=8.1 Hz), 7.73 (s, 1H), 7.98 (d, J=8.1, 1H), 11.6 (bs, 1H). Anal. Cald. for $C_{15}H_{14}BrNO_4$: C, 51.16; H, 4.01; N, 3.98. Found: C, 50.83; H, 4.02; N, 4.00.

Synthesis of methyl 3-(4-(2,4-difluorobenzyloxy)-3-bromo-6-methyl-2-oxopyridin-1(2H)-yl)-4-methylbenzoate (3)

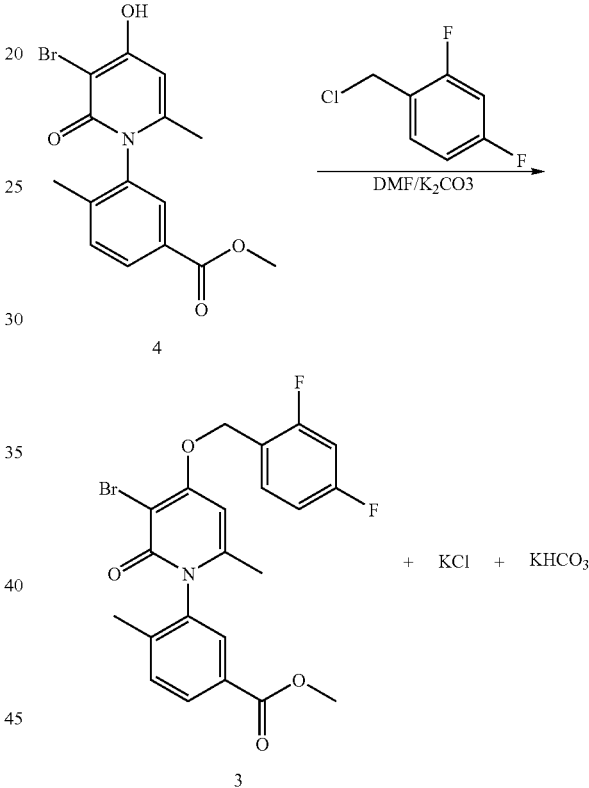

Methyl 3-(3-bromo-4-hydroxy-6-methyl-2-oxopyridin-1 (2H)-yl)-4-methylbenzoate (4) (1.9 kg, 5.4 moles), N,N-dimethylformamide (4.8 L) and powdered $K_2CO_3$ (1.1 kg, 8.1 moles) were mixed together and heated to 55° C. under nitrogen. 2,4-difluorobenzyl chloride (964 g, 5.9 moles) was added at a rate such that the temperature was maintained below 65° C. After the addition, the mixture was heated at 65° C. for 3.5 hours. After 3 hours the reaction was complete and the reaction mixture was cooled to 20-25° C. with the addition of 19 L water. The solid was filtered and washed with 15 L water. The crude product was then purified by trituration in refluxing methanol (4 L). The mixture was cooled and the solid filtered to yield 2.32 kg (90%) product. $^1$H NMR (300 MHz, CDCl$_3$) δ 1.90 (s, 3H), 2.11 (s, 3H), 3.87 (s, 3H), 5.25 (s, 2H), 6.11 (s, 1H), 6.88 (dt, J=4.8, 1.8 Hz, 1H), 6.96 (t, J=4.8 Hz, 1H), 7.42 (d, J=6 Hz, 1H), 7.59 (q, J=4.8 Hz, 1H), 7.74 (s, 1H), 8.02 (d, J=6 Hz, 1H). Anal. Cald. for $C_{22}H_{18}BrF_2NO_4$: C, 55.25; H, 3.79; N, 2.93. Found: C, 55.34; H, 3.83; N, 3.14.

Preparation of 3-(4-(2,4-difluorobenzyloxy)-3-bromo-6-methyl-2-oxopyridin-1(2H)-yl)-4-methylbenzoic acid (2)

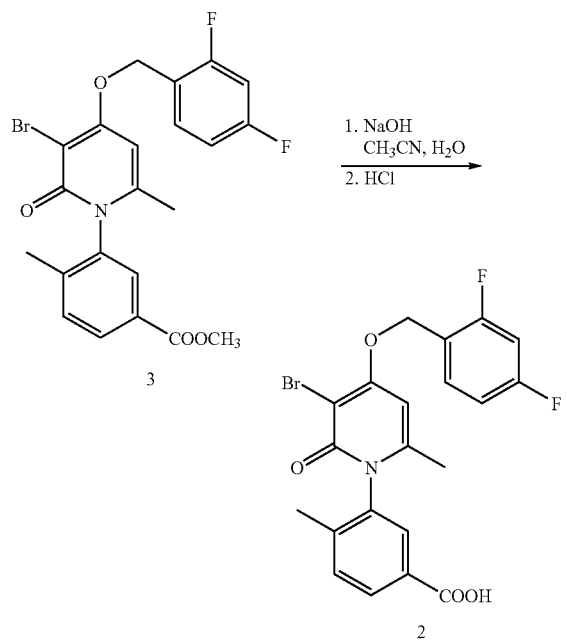

Methyl 3-(4-(2,4-difluorobenzyloxy)-3-bromo-6-methyl-2-oxopyridin-1(2H)-yl)-4-methylbenzoate (3) (3.4 kg, 7.1 moles), 2.5M NaOH (3.1 L. 7.8 moles), CH$_3$CN (12 L) and 8.6 L water were mixed together and heated to 60° C., under nitrogen. Once the mixture became homogeneous the mixture was stirred for an additional hour. The reaction mixture was cooled to 20° C. and then treated with 865 ml concentrated HCl at a rate such that the temperature was maintained below 25° C. After the HCl addition was completed the mixture was stirred for another hour. The product was filtered and washed with 12 L CH$_3$CN, dried to give 2.87 kg (87%) adduct. $^1$H NMR (300 MHz, CD$_3$OD) δ 7.87 (dd, J=7.8, 1.6 Hz, 1H), 7.82 (d, J=1.8 Hz, 1H), 7.69 (q, J=8.1 Hz, 1H), 7.57 (d, J=8.1 Hz, 1H), 7.09 (dt, J=2.2, 8.6 Hz, 1H), 6.7 (s, 1H), 5.4 (s, 2H), 2.14 (s, 3H), 2.02 (s, 3H) (d, J=2.4 Hz, 1H), 3.94 (s, 3H), 2.15 (s, 3H), 1.91 (s, 3H). ES-HRMS m/z 464.0275 (M+H calcd for C$_{21}$H$_{17}$BrF$_2$NO$_4$ requires 464.0304). Anal. Cald. for C$_{21}$H$_{16}$BrF$_2$NO$_4$: C, 54.33; H, 3.47; N, 3.02. Found: C, 54.40; H, 3.42; N, 3.17

Preparation of (−)3-(4-(2,4-difluorobenzyloxy)-3-bromo-6-methyl-2-oxopyridin-1(2H)-yl)-N,4-dimethylbenzamide (1)

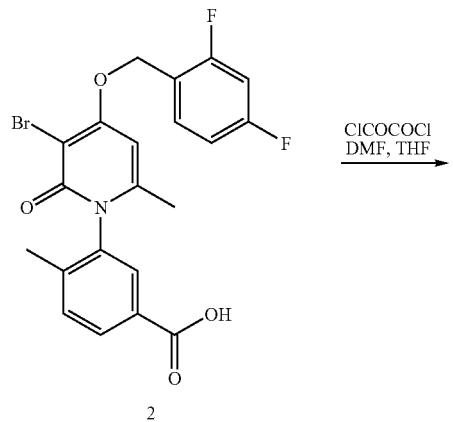

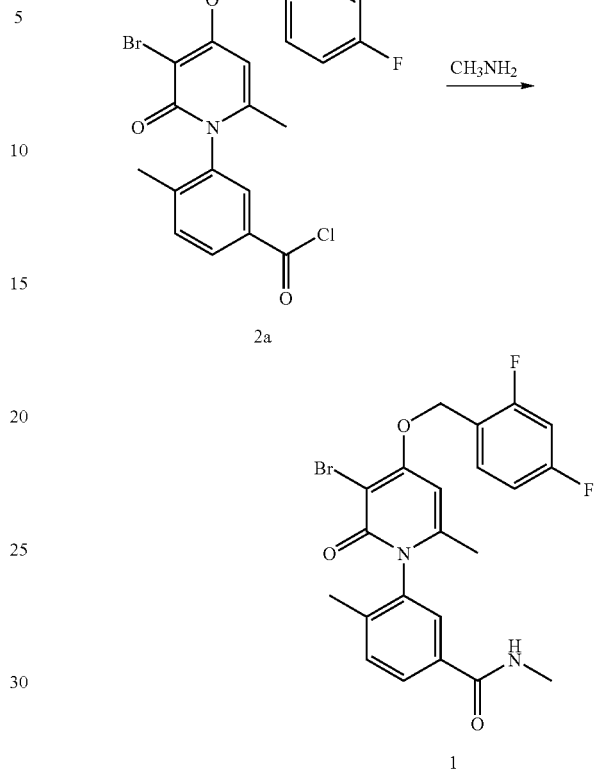

3-(4-(2,4-difluorobenzyloxy)-3-bromo-6-methyl-2-oxopyridin-1(2H)-yl)-4-methylbenzoic acid (2)(1.4 kg, 3.0 moles) was suspended in 7 L tetrahydrofuran with 28 ml N,N-dimethylformamide and chilled to 5° C. Oxalyl chloride (368 ml, 4.22 moles) was added to the reactor at a rate such that the temperature was maintained below 10° C. and the gas evolution was under control. After the oxalyl chloride had been added the reaction mixture was allowed to warm to room temperature. The reaction was completed when the mixture became homogeneous. The reaction mixture was drained into separate container and set aside. 40% methylamine (4.4 L, 50.3 moles) and 2.6 L water were added to the reactor and chilled to below 5° C. The reaction mixture was then added to the chilled methylamine solution at a rate such that the temperature was maintained below 15° C. Once the addition was completed the mixture was allowed to warm to room temperature and stirred an additional 30 minutes. 12.6 L water was added to the mixture and the stirring was continued for another hour. The product was filtered and washed with 10 L water to give 1.25 kg (90%). $^1$H NMR (300 MHz, DMSO-d$_6$) δ 7.95 (bs, 1H), 7.88 (dd, J=1.2, 5.7 Hz, 1H), 7.68 (q, J=5.1 Hz, 1H), 7.64 (d, J=1.2 Hz, 1H), 7.46 (d, J=6.0 Hz, 1H), 7.36 (bs, 1H), 7.29 (dt, J=1.8, 7.8 Hz, 1H), 7.16 (dt, J=1.8, 76.0 Hz, 1H), 6.70 (s, 1H), 6.18 (s, 1H), 5.33 (s, 2H), 3.32 (s, 3H), 1.97 (s, 3H), 1.88 (s, 3H). Anal. Cald. for C$_{21}$H$_{17}$BrF$_2$N$_2$O$_3$+0.66 EtOH+0.1H$_2$O: C, 54.11; H, 4.30; N, 5.65. Found: C, 54.03; H, 4.59; N, 5.79.

The racemic product 3-(4-(2,4-difluorobenzyloxy)-3-bromo-6-methyl-2-oxopyridin-1(2H)-yl)-N,4-dimethylbenzamide (1) produced was then chromatographed using a chiral stationary phase such as Chiralcel OJ™ or Chiralpak® AD™ (Daicel Chemical Industries, Japan) with methanol or ethanol as the mobile phase to isolate the corresponding (−)-

3-(4-(2,4-difluorobenzyloxy)-3-bromo-6-methyl-2-oxopyridin-1(2H)-yl)-N,4-dimethylbenzamide (1).

Example 2

Scheme 9 depicts the overall synthesis that is described in Example 2.

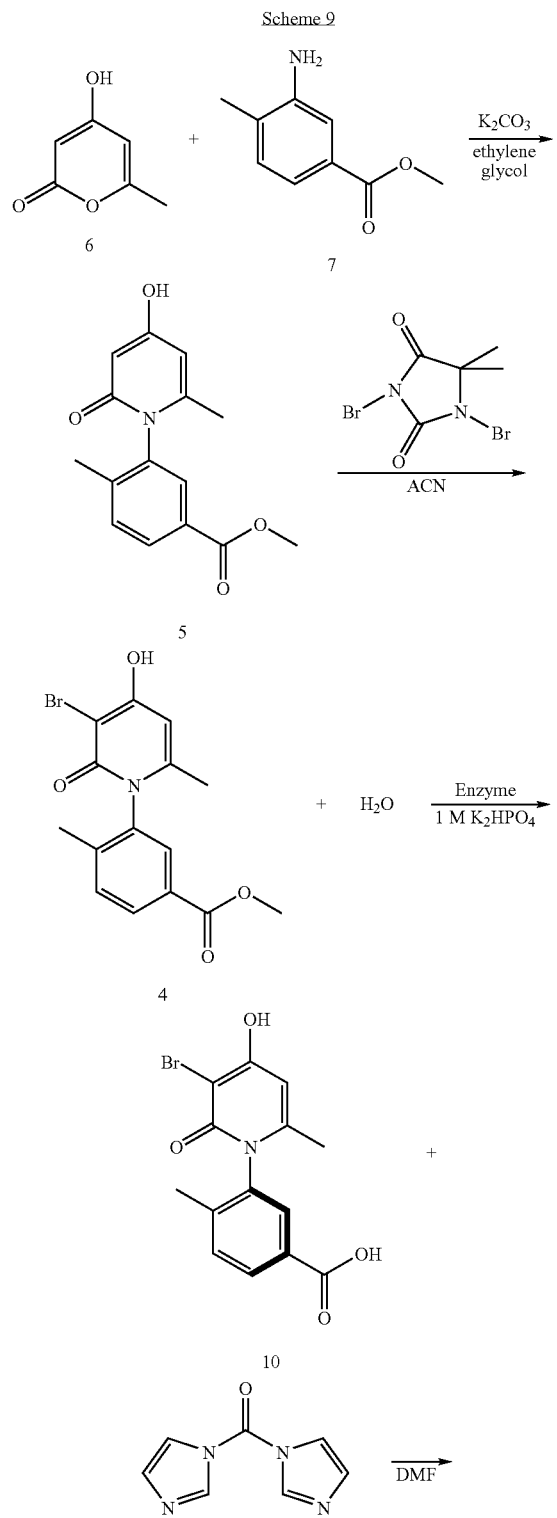

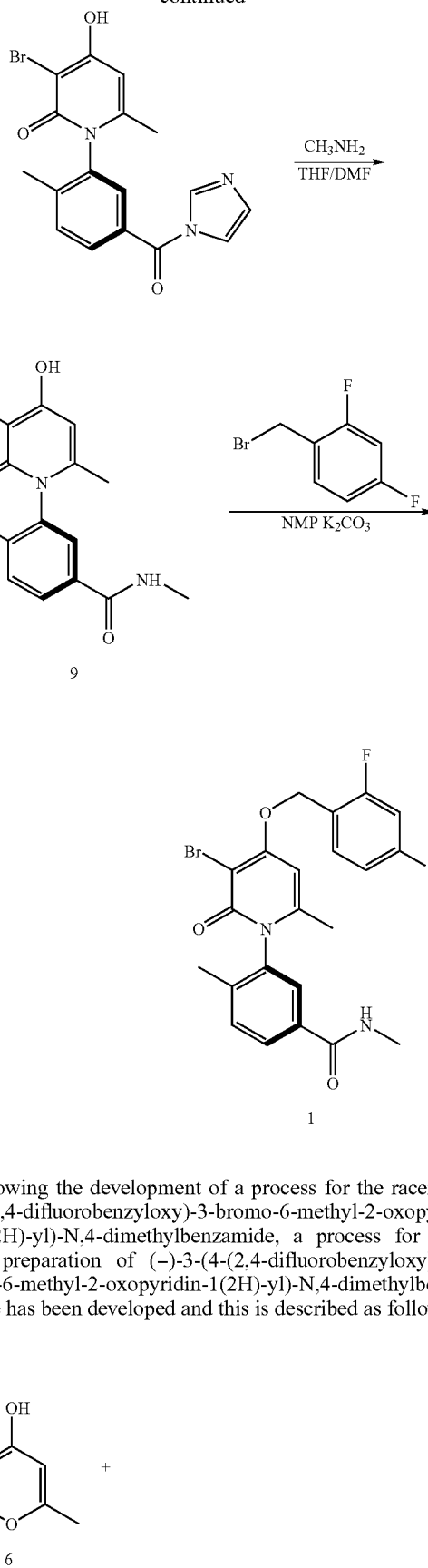

Following the development of a process for the racemic 3-(4-(2,4-difluorobenzyloxy)-3-bromo-6-methyl-2-oxopyridin-1(2H)-yl)-N,4-dimethylbenzamide, a process for the direct preparation of (−)-3-(4-(2,4-difluorobenzyloxy)-3-bromo-6-methyl-2-oxopyridin-1(2H)-yl)-N,4-dimethylbenzamide has been developed and this is described as follows:

Step 1

-continued

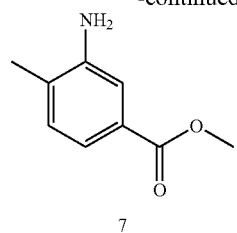
7

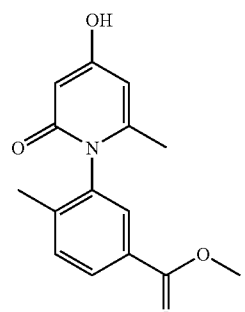
5

+ H₂O 4-hydroxy-6-methylpyranone (6) (6.71 kg, 53.2 moles), methyl-3-amino-4-methyl benzoate (7) (4.50 kg. 27.2 moles), catalytic K₂CO₃ (0.54 kg, 3.91 moles), acetonitrile (6.14 L) and ethylene glycol (6.14 L) were mixed under nitrogen and the acetonitrile was removed by vacuum distillation. The reaction was stirred for 18-24 hours at 65° C. Following the reaction the mixture was cooled to 25° C. A 1:1 acetonitrile/water solution (6.14 L each) was added to the mixture. The mixture was stirred for 90 minutes and cooled to 0° C. A product was colleted, washed with a 1:1 acetonitrile/water solution (3.4 L each) and dried to give 60% isolated yield of methyl 3-(4-hydroxy-6-methyl-2-oxopyridin-1(2H)-yl)-4-methylbenzoate (5).

Step 2

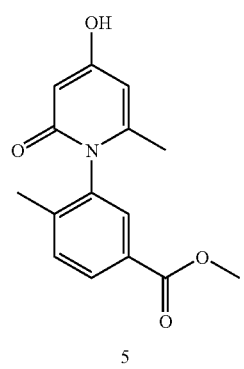
5

+

-continued

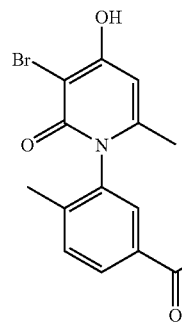
4

+

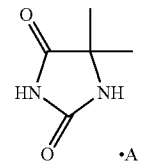
·A

A solution of 1,3-dibromo-5,5-dimethylhydantoin (1.375 kg. 4.81 moles) in acetonitrile (11.5 L) was added to a solution of methyl 3-(4-hydroxy-6-methyl-2-oxopyridin-1(2H)-yl)-4-methylbenzoate (5) (2.50 kg, 9.15 mol) in acetonitrile (4.8 L). The solution was added at a rate that maintained the temperature less than −10° C. for 90 to 180 minutes. A portion of the acetonitrile (approximately 6 L) was removed after completion of the reaction via distillation. The product was precipitated by the addition of water (7.9 L) and filtered to yield 2.90 kg (90%) of methyl 3-(3-bromo-4-hydroxy-6-methyl-2-oxopyridin-1(2H)-yl)-4-methylbenzoate (4)

Step 3

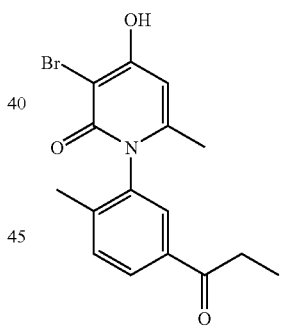
4

+ H₂O $\xrightarrow{\text{Enzyme}}{\text{1M K}_2\text{HPO}_4}$

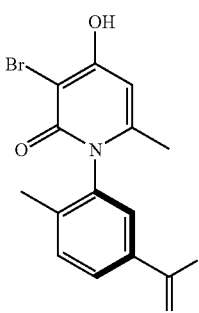
10

+

-continued

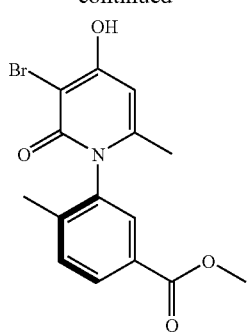 + CH₃OH

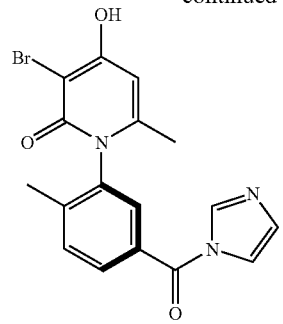 $\xrightarrow[\text{THF/DMF}]{\text{CH}_3\text{NH}_2}$

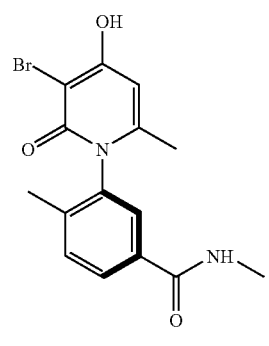

9

(+/−)Methyl 3-(3-bromo-4-hydroxy-6-methyl-2-oxopyridin-1(2H)-yl)-4-methylbenzoate (4) (1 kg, 2.84 moles) was mixed with 1M dibasic potassium phosphate buffer solution (dibasic potassium phosphate (3.05 kg, 17.5 moles) and water (16.4 L)) and warmed to 25° C. The pH of the solution was adjusted to 9.1 with 10% NaOH solution (about 4.2 L) followed by the addition of Savinase® enzyme (Novozyme, Bagsvaerd, Denmark) and warmed to 30° C. After stirring for about 40-45 hours, the pH of the solution was adjusted to 6.0 using 6N HCl (2.3 L) and stirred for 30 minutes. The resulting precipitate was the unreacted enantiomer of the ester methyl (+)3-(3-bromo-4-hydroxy-6-methyl-2-oxopyridin-1(2H)-yl)-4-methylbenzoate (423 gm), which was isolated by filtration and washed with water. The aqueous filtrate was washed with 5.0 L methylene chloride. It was then further acidified to pH 3.6 with 2.1 L of 6N HCl to precipitate and isolate the optically enriched acid (−)3-(3-bromo-4-hydroxy-6-methyl-2-oxopyridin-1(2H)-yl)-4-methylbenzoic acid (10) by filtration. 1.3 kg (80% of theory) of product was obtained after drying.

Step 4

(−)3-(3-bromo-4-hydroxy-6-methyl-2-oxopyridin-1(2H)-yl)-4-methylbenzoic acid (10) (1.50 kg, 4.44 moles), 1,1′-carbonyldiimidazole (1.08 kg, 6.66 moles) and N,N-dimethylformamide (3 mL) were mixed together at ambient temperature. Once the activation reaction was deemed complete, 2 M methylamine solution in tetrahydrofuran (5.5 L, 11.1 moles) was added at a rate that maintained the temperature below 30° C. The mixture became homogeneous as the reaction reached completion. A solution of 1 N hydrochloric acid solution (15.4 kg) was added to reach pH 3 or less. The acidification precipitated the product. The product was filtered, washed with water and vacuum dried at 60° C. overnight to give (−)3-(3-bromo-4-hydroxy-6-methyl-2-oxopyridin-1(2H)-yl)-N,4-dimethylbenzamide (9) (1.56 kg, 4.44 moles, 97% purity).

Step 5

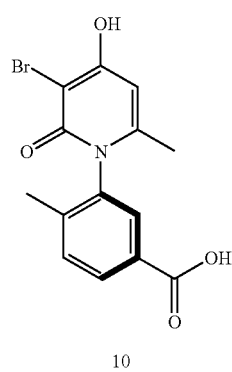 +

10

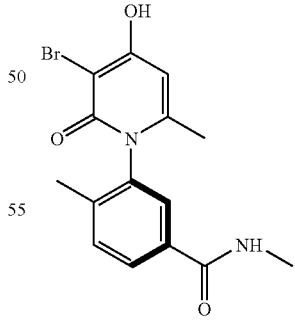 +

9

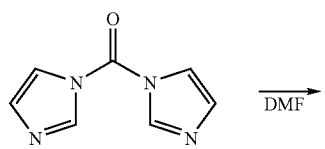 $\xrightarrow{\text{DMF}}$

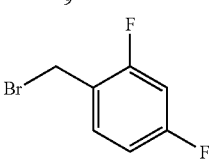 + K₂CO₃ $\xrightarrow{\text{NMP}}$

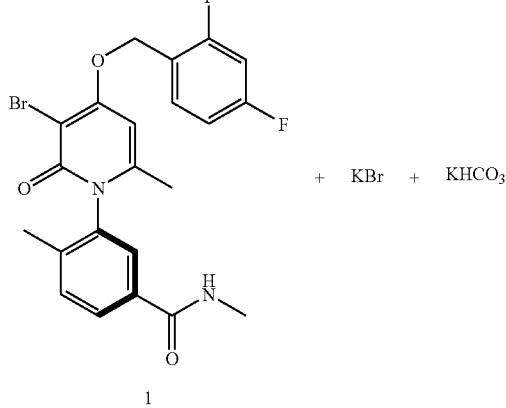

+ KBr + KHCO₃

3-(3-bromo-4-hydroxy-6-methyl-2-oxopyridin-1(2H)-yl)-N,4-dimethylbenzamide (9) (1 kg, 2.85 moles), potassium carbonate (0.43 kg, 3.11 moles), 1-methyl-2-pyrrolidinone (4.0 L) and 2,4-difluorobenzyl bromide (0.71 kg, 3.42 moles) were mixed together and heated at 30° C. for 2 hours. The reaction mixture was diluted with water (12.5 L) over a period of 30 to 60 minutes and then stirred for 30 to 60 minutes. The product was filtered and washed with water. (−)-3-(4-(2,4-difluorobenzyloxy)-3-bromo-6-methyl-2-oxopyridin-1(2H)-yl)-N,4-dimethylbenzamide (1) (1.36 kg, 95% purity, greater than 99% ee) was obtained.

The product was then purified. (−)-3-(4-(2,4-difluorobenzyloxy)-3-bromo-6-methyl-2-oxopyridin-1(2H)-yl)-N,4-dimethylbenzamide (1) (4.0 kg, 8.4 moles) and methanol (13 L) were mixed together and brought to 60° C. and stirred for 1 hour. The product was filtered and washed with ambient temperature methanol (3.0 L) to give (−)-3-(4-(2,4-difluorobenzyloxy)-3-bromo-6-methyl-2-oxopyridin-1(2H)-yl)-N,4-dimethylbenzamide (1) (2.9 kg, 6.1 moles, 98.4% purity).

The above detailed description of embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

What is claimed is:

1. A process for preparing (−)-3-(4-(2,4-difluorobenzyloxy)-3-bromo-6-methyl-2-oxopyridin-1(2H)-yl)-N,4-dimethylbenzamide, or a pharmaceutically acceptable salt thereof comprising the steps:

a) contacting a compound of formula V:

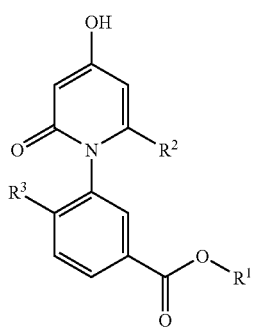

with a brominating reagent in the presence of at least one solvent to produce a compound of Formula IV:

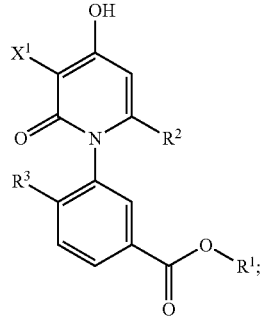

b) contacting a compound of Formula IV with a hydrolase in the presence of a buffer solution to produce a compond of Formula X:

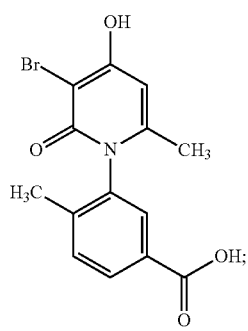

c) contacting a compound of Formula X with an activating reagent in the presence of at least one solvent and then contacting the resulting mixture with methylamine to produce a compound of Formula IX:

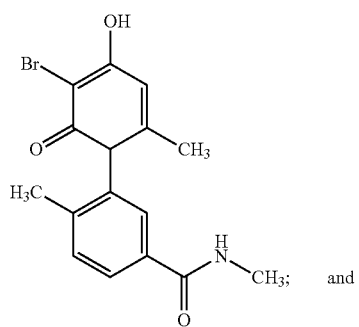

and d) contacting a compound of Formula IX with a 2,4-difluorobenzylhalide in the presence of a base and at least one solvent;
wherein
$R^1$ is a $C_1$-$C_6$ alkyl or aryl.

2. The process of claim 1 wherein (−)-3-(4-(2,4-difluorobenzyloxy)-3-bromo-6-methyl-2-oxopyridin-1(2H)-yl)-N,4-dimethylbenzamide is present in enantiomeric excess of 80%.

3. The process of claim 1 wherein the halogenating reagent, in step a, is 1,3-dibromo-5,5-dimethylhydantoin.

4. The process of claim 1 wherein the solvent, in step a, is acetonitrile, acetic acid, or acetic acid containing water, a lower alkyl alcohol, or dioxane.

5. The process of claim 1 wherein the hydrolase, in step b, is a *Bacillus* sp. protease.

6. The process of claim 1 wherein the buffer solution, in step b, is a dibasic potassium phosphate buffer solution or an inorganic bicarbonate buffer solution.

7. The process of claim 1 wherein the activating reagent, in step c, is 1,1'-carbonyldiimidazole.

8. The process of claim 1 wherein the solvent, in step c, is dimethylformamide, dichloroethane, tetrahydrofuran, dioxane, methyl tert-butyl ether, or toluene.

9. The process of claim 1 wherein the solvent, in step d, is N-methylpyrrolidinone.

10. The process of claim 1 wherein the base, in step d, is potassium carbonate.

* * * * *